United States Patent
Kawana et al.

(10) Patent No.: US 11,400,030 B2
(45) Date of Patent: Aug. 2, 2022

(54) TWO-PASTE DENTAL CURABLE COMPOSITION

(71) Applicant: KURARAY NORITAKE DENTAL INC., Kurashiki (JP)

(72) Inventors: Mariko Kawana, Niigata (JP); Kenji Hatanaka, Ibaraki (JP); Momoe Abe, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 0 days.

(21) Appl. No.: 16/626,675

(22) PCT Filed: Jun. 28, 2018

(86) PCT No.: PCT/JP2018/024700
§ 371 (c)(1),
(2) Date: Dec. 26, 2019

(87) PCT Pub. No.: WO2019/004391
PCT Pub. Date: Jan. 3, 2019

(65) Prior Publication Data
US 2020/0155421 A1 May 21, 2020

(30) Foreign Application Priority Data
Jun. 28, 2017 (JP) .............................. JP2017-126707

(51) Int. Cl.
*A61K 6/887* (2020.01)
*A61K 6/77* (2020.01)

(52) U.S. Cl.
CPC ................ *A61K 6/887* (2020.01); *A61K 6/77* (2020.01)

(58) Field of Classification Search
CPC .................................................. A61K 6/887
See application file for complete search history.

(56) References Cited

U.S. PATENT DOCUMENTS

| 5,192,815 | A | * | 3/1993 | Okada | ........................ | C07F 7/10 |
| | | | | | | 523/115 |
| 2010/0010115 | A1 | | 1/2010 | Kohro et al. | | |

FOREIGN PATENT DOCUMENTS

| EP | 0 368 657 A2 | | 5/1990 |
|---|---|---|---|
| JP | 63-51308 A | | 3/1988 |
| JP | 4-18453 A | | 1/1992 |
| JP | 2007-153957 A | | 6/2007 |
| JP | 2007153957 A | * | 6/2007 |
| JP | 2010-18524 A | | 1/2010 |
| JP | 2010-168489 A | | 8/2010 |
| JP | 2015-105324 A | | 6/2015 |
| JP | 2016-124811 A | | 7/2016 |

OTHER PUBLICATIONS

English machine translation of Nakahara et al. (JP 2007-153957) (Year: 2007).*
International Search Report dated Aug. 7, 2018 in PCT/JP2018/024700 filed on Jun. 28, 2018, 1 page.
Maruo, Y. et al., "Does 8-methacryloxyoctyl trimethoxy silane (8-MOTS) improve initial bond strength on lithium disilicate glass ceramic?" Dental Materials, vol. 33, No. 3, 2017, pp. e95-e100.
Extended European Search Report dated Dec. 11, 2020 in European Patent Application No. 18823843.0, 7 pages.

* cited by examiner

*Primary Examiner* — Michael F Pepitone
(74) *Attorney, Agent, or Firm* — Oblon, McClelland, Maier & Neustadt, L.L.P.

(57) ABSTRACT

The present invention provides a two-paste dental curable composition achieving clinically acceptable bond durability to dental adherends including dental glass ceramic restorations (particularly lithium disilicate-containing glass ceramic restorations) without using conventionally used primers. The present invention relates to a two-paste dental curable composition comprising: a first agent comprising a polymerizable monomer (a) having an acid group, a polymerizable monomer (b) having no acid group, a polymerization initiator (c), and a filler (d); and a second agent comprising a polymerizable monomer (b) having no acid group, at least one filler (e) selected from the group consisting of a basic glass filler and alumina, a polymerization accelerator (f), and a silane coupling agent (g) represented by the following general formula [I]:

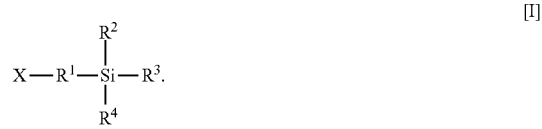

(The definitions of the symbols are omitted.)

20 Claims, No Drawings

TWO-PASTE DENTAL CURABLE COMPOSITION

CROSS REFERENCE TO RELATED APPLICATIONS

The present application is the national stage of international application PCT/JP2018/024700, filed on Jun. 28, 2018, and claims the benefit of the filing date of Japanese 2017-126707, filed on Jun. 28, 2017, the entire content of each of which, to the extent allowed, is incorporated by reference herein.

TECHNICAL FIELD

The present invention relates to a self-adhesive two-paste dental curable composition. The present invention particularly relates to a two-paste dental curable composition achieving clinically acceptable bond durability to dental glass ceramic restorations, particularly lithium disilicate-containing glass ceramic restorations, without using conventionally used primers.

BACKGROUND ART

Adhesive materials are used for restorative treatment of moist matter, for example, biological hard tissues such as tooth structures and bones. Curable resin compositions composed of a radical polymerizable monomer, polymerization initiator, etc. are widely used as adhesive materials used for moist matter.

A tooth that lost its function due to dental caries or an accident is repaired, for example, by fixing a tooth crown restorative material which is called an inlay or crown and made of a metal or ceramic to the tooth. An adhesive called a dental cement is used for such fixation of a tooth crown restorative material to a tooth.

Conventionally, either a tooth structure or tooth crown restorative material has to be subjected to a primer treatment suitable for the material as a treatment preceding adhesion with a dental cement, and it is essential for dental glass ceramic materials to be subjected to a silane treatment with a silane coupling agent after an etching treatment. Therefore, in terms of reducing such complicated operation, a dental curable composition (Patent Literature 1), self-adhesive resin cement (Patent Literature 2), and the like have been proposed that achieve clinically acceptable adhesiveness without using a primer. Additionally, in terms of improving the bond durability to dental glass ceramic materials, a dental adhesive composition that can be used as a primer and an adhesive has also been proposed (Patent Literature 3).

In recent years, lithium disilicate glass is becoming common as a dental glass ceramic excellent in aesthetic quality and strength. There is a problem in that even a silane treatment of the surface of lithium disilicate glass with a silane coupling agent does not make it easy to achieve high bond durability. Therefore, to achieve long-lasting good bond durability to lithium disilicate glass, mechanical interlocking force achieved by surface roughening by means of a hydrofluoric acid treatment or sandblasting treatment is needed in addition to the chemical adhesion achieved by a silane coupling agent. As just described, high bond durability to dental glass ceramics such as lithium disilicate glass is achieved by very complicated adhesion operation. Since dental treatment generally requires simple and quick adhesion operation, a self-adhesive cement for which the above treatments are unnecessary and which has good bond durability has been demanded.

CITATION LIST

Patent Literature

Patent Literature 1: JP 2016-124811 A
Patent Literature 2: JP 2010-018524 A
Patent Literature 3: JP S63-051308 A

SUMMARY OF INVENTION

Technical Problem

Patent Literature 1 discloses a two-paste dental curable composition achieving clinically acceptable bond durability to all dental adherends including dental glass ceramic restorations without using conventionally used primers and being excellent in bond strength after long-term storage and in stability of the paste properties. However, Patent Literature 1 makes no statement on the bond durability to lithium disilicate-containing glass ceramics. Moreover, good bond durability to lithium disilicate glass cannot be achieved with the use of the silane coupling agents shown in Examples of Patent Literature 1.

Patent Literature 2 discloses a dental cement composition that is self-adhesive to various adherends. However, Patent Literature 2 makes no statement on addition of a silane coupling agent for the purpose of achieving the adhesiveness to dental glass ceramic materials.

Patent Literature 3 discloses a composition composed of a silane coupling agent and acid group-containing polymerizable monomer and used to adhere dental glass ceramics. However, Patent Literature 3 makes no statement on the bond durability to lithium disilicate-containing glass ceramics.

The present invention aims to provide a two-paste dental curable composition achieving clinically acceptable bond durability to dental adherends including dental glass ceramic restorations, particularly lithium disilicate-containing glass ceramic restorations, without using conventionally used primers.

Solution to Problem

The present inventors have made a detailed study of a two-paste dental curable composition achieving clinically acceptable bond durability to dental adherends including dental glass ceramic restorations, particularly lithium disilicate-containing glass ceramic restorations, without using conventionally used primers. As a result, the present inventors have found that: a siloxane bond at an adhesive interface on the surface of lithium disilicate glass is likely to be hydrolyzed; lithium disilicate glass is unlikely to be roughened by an acid compared to, for example, porcelain which is a conventional silica-based glass ceramic; and the above problems can be solved by a certain two-paste dental curable composition comprising a silane coupling agent having a certain structure, and have completed the present invention.

That is, the present invention includes the following aspects.

[1] A two-paste dental curable composition comprising:
a first agent comprising a polymerizable monomer (a) having an acid group, a polymerizable monomer (b) having no acid group, a polymerization initiator (c), and a filler (d); and a second agent comprising a polymerizable monomer (b) having no acid group, at least one filler (e) selected from the group consisting of a basic glass filler and alumina, a polymerization accelerator (f), and a silane coupling agent (g) represented by the following general formula [I];

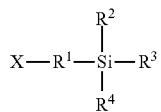

[I]

wherein X represents a polymerizable functional group selected from the group consisting of a (meth)acryloxy group, a vinyl group, and an epoxy group, $R^1$ represents a divalent aliphatic group optionally having a divalent group and having a linear chain having a carbon chain length of 5 or more or a divalent aromatic group optionally having a divalent group and having 6 or more carbon atoms, $R^2$, $R^3$, and $R^4$ are each independently a hydroxy group, an alkyl group having 1 to 5 carbon atoms, or an alkoxy group having 1 to 5 carbon atoms, and at least one of $R^2$, $R^3$, and $R^4$ is an alkoxy group having 1 to 5 carbon atoms.

[2] The two-paste dental curable composition according to wherein $R^1$ is a divalent aliphatic group optionally having a divalent group and having a linear chain having a carbon chain length of 7 or more or a divalent aromatic group optionally having a divalent group and having 7 or more carbon atoms.

[3] The two-paste dental curable composition according to [1] or [2], wherein
$R^2$, $R^3$, and $R^4$ are each independently a hydroxy group, an alkyl group having 1 to 3 carbon atoms, or an alkoxy group having 1 to 3 carbon atoms and at least one of $R^2$, $R^3$, and $R^4$ is an alkoxy group having 1 to 3 carbon atoms.

[4] The two-paste dental curable composition according to any one of [1] to [3], wherein
$R^2$, $R^3$, and $R^4$ are each independently a hydroxy group, a methyl group, or a methoxy group and at least one of $R^2$, $R^3$, and $R^4$ is a methoxy group.

[5] The two-paste dental curable composition according to any one of [1] to [4], wherein $R^2$, $R^3$, and $R^4$ are each a methoxy group.

[6] The two-paste dental curable composition according to any one of [1] to [5], wherein $R^4$ is a divalent aliphatic group optionally having a divalent group and having a linear chain having a carbon chain length of 8 or more.

[7] The two-paste dental curable composition according to any one of [1] to [5], wherein $R^4$ is a divalent aliphatic group optionally having a divalent group and having 8 or more carbon atoms.

[8] The two-paste dental curable composition according to any one of [1] to [7], wherein the silane coupling agent (g) is at least one selected from the group consisting of 5-(meth)acryloxypentyltrimethoxysilane, 6-(meth)acryloxyhexyltrimethoxysilane, 7-(meth)acryloxyheptyltrimethoxysilane, 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, 8-(meth)acryloxyoctylmethyldimethoxysilane, 10-(meth)acryloxydecylmethyldimethoxysilane, 11-(meth)acryloxyundecylmethyldimethoxysilane, and (meth)acryloxymethylphenethyltrimethoxysilane.

[9] The two-paste dental curable composition according to any one of [1] to [7], wherein the silane coupling agent (g) is at least one selected from the group consisting of 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, and (meth)acryloxymethylphenethyltrimethoxysilane.

[10] The two-paste dental curable composition according to any one of [1] to [9], wherein
the second agent further comprises a crosslinking agent (h) and the crosslinking agent (h) is a compound represented by the following general formula [V]:

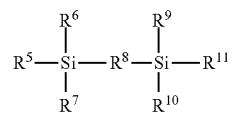

[V]

and/or a compound represented by the general formula [VI]:

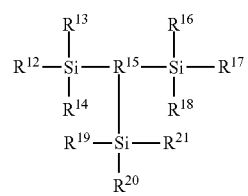

[VI]

wherein $R^8$ represents a divalent aliphatic group optionally having a divalent group and having a carbon chain length of 1 or more or a divalent aromatic group optionally having a divalent group and having 6 or more carbon atoms, $R^{15}$ represents a trivalent aliphatic group having a carbon chain length of 1 or more or a trivalent aromatic group optionally having a divalent group and having 6 or more carbon atoms, and $R^5$ to $R^7$, $R^9$ to $R^{14}$, and $R^{16}$ to $R^{21}$ each independently represent a hydroxy group or an alkoxy group having 1 to 5 carbon atoms.

[11] The two-paste dental curable composition according to [10], wherein
$R^8$ is a divalent aromatic group optionally having a divalent group and having 6 or more carbon atoms and
$R^{15}$ is a trivalent aromatic group optionally having a divalent group and having 6 or more carbon atoms.

[12] The two-paste dental curable composition according to [10], wherein
the crosslinking agent (h) is the compound represented by the general formula [V] and
$R^8$ is a divalent aliphatic group optionally having a divalent group and having a carbon chain length of 1 or more.

[13] The two-paste dental curable composition according to any one of [1] to [12], wherein the first agent further comprises a silanol condensation catalyst (i) represented by the following general formula [VII]:

$$M(R^{22})_n$$ [VII]

wherein M represents Ti, Zr, or Al, $R^{22}$ represents an aliphatic group, n represents an integer of 1 to 4, and when there are two or more $R^{22}$, the two or more R22 may be the same as or different from each other.

[14] The two-paste dental curable composition according to [13], wherein $R^{22}$ is an alkoxy group having 1 to 9 carbon atoms, an acyloxy group having 2 to 9 carbon atoms, an alkenyloxy group having 3 to 9 carbon atoms, a β-diketonate group having 5 to 15 carbon atoms, or a diacylmethyl group having acyl groups each having 1 to 9 carbon atoms.

[15] The two-paste dental curable composition according to any one of [1] to [14], wherein at least one of the first agent and the second agent further comprises a photopolymerization initiator (j).

[16] The two-paste dental curable composition according to any one of [1] to [15], wherein the filler (e) is barium glass and/or alumina.

Advantageous Effects of Invention

The two-paste dental curable composition of the present invention achieves clinically acceptable bond durability to dental adherends including dental glass ceramic restorations (particularly lithium disilicate-containing glass ceramic restorations) without using conventionally used primers. Moreover, since the two-paste dental curable composition of the present invention can achieve clinically acceptable bond durability without using a primer, the two-paste dental curable composition of the present invention does not require complicated operation.

DESCRIPTION OF EMBODIMENTS

A first agent of a two-paste dental curable composition of the present invention comprises a polymerizable monomer (a) having an acid group, a polymerizable monomer (b) having no acid group, a polymerization initiator (c), and a filler (d).

The first agent of the two-paste dental curable composition of the present invention comprises the polymerizable monomer (a) having an acid group (this monomer is hereinafter referred to as "acid group-containing polymerizable monomer (a)"). Addition of the acid group-containing polymerizable monomer (a) can provide the two-paste dental curable composition with the adhesiveness to tooth structures and dental prosthetic materials.

Examples of the acid group-containing polymerizable monomer (a) include polymerizable monomers having at least one acid group such as a phosphoric acid group, pyrophosphoric acid group, thiophosphoric acid group, phosphonic acid group, sulfonic acid group, or carboxylic acid group and further having at least one polymerizable group such as an acryloyl group, methacryloyl group, vinyl group, or styrene group. The acid group-containing polymerizable monomer (a) has compatibility with adherends and has a demineralization effect on tooth structures. Specific examples of the acid group-containing polymerizable monomer (a) will be presented below. It should be noted that the term "(meth)acryl" as used herein collectively refers to "acryl" and "methacryl," and the term "(meth)acryloxy" as used herein collectively refers to "acryloxy" and "methacryloxy."

Examples of the phosphoric acid group-containing polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl] hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl] hydrogen phosphate; and their acid chlorides, alkali metal salts, and ammonium salts.

Examples of the pyrophosphoric acid group-containing polymerizable monomer include: bis[2-(meth)acryloyloxyethyl] pyrophosphate, bis[4-(meth)acryloyloxybutyl] pyrophosphate, bis[6-(meth)acryloyloxyhexyl] pyrophosphate, bis[8-(meth)acryloyloxyoctyl] pyrophosphate, and bis[10-(meth)acryloyloxydecyl] pyrophosphate; and their acid chlorides, alkali metal salts, and ammonium salts.

Examples of the thiophosphoric acid group-containing polymerizable monomer include: 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, and 20-(meth)acryloyloxyeicosyl dihydrogen thiophosphate; and their acid chlorides, alkali metal salts, and ammonium salts.

Examples of the phosphonic acid group-containing polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth)acryloyloxydecylphosphonoacetate; and their acid chlorides, alkali metal salts, and ammonium salts.

Examples of the sulfonic acid group-containing polymerizable monomer include 2-(meth)acrylamido-2-methylpropanesulfonic acid, styrenesulfonic acid, and 2-sulfoethyl (meth)acrylate.

Examples of the carboxylic acid group-containing polymerizable monomer include a polymerizable monomer having one carboxy group per molecule and a polymerizable monomer having a plurality of carboxy groups per molecule.

Examples of the polymerizable monomer having one carboxy group per molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and their acid halides.

Examples of the polymerizable monomer having a plurality of carboxy groups per molecule include: 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydecane-1,1-clicarboxylic acid, 13-(meth)acryloyloxytridecane-1,1-dicarboxylic acid, 4-(meth)acryloyloxyethyl trimellit ate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, and 2-(meth)acryloyloxyethyl-3'-(meth)acryloyloxy-2'-(3,4-dicarboxybenzoyloxy)propyl succinate; and their acid anhydrides and acid halides.

One of the above acid group-containing polymerizable monomers (a) may be used alone, or two or more thereof may be used in combination. Among these acid group-containing polymerizable monomers (a), in view of high bond strength to dental adherends, preferred is at least one selected from the group consisting of the phosphoric acid group-containing polymerizable monomers, carboxylic acid group-containing polymerizable monomers, and sulfonic acid group-containing polymerizable monomers, more preferred is at least one selected from the group consisting of phosphoric acid group-containing polymerizable monomers having two or more hydroxy groups bonded to a phosphorus atom, the polymerizable monomers having a plurality of carboxy groups per molecule, and sulfonic acid group-containing polymerizable monomers, and even more preferred is at least one selected from the group consisting of 10-(meth)acryloyloxydecyl dihydrogen phosphate, 1,3-di(meth)acryloyloxypropyl dihydrogen phosphate, 2-(meth)acryloyloxyethyl dihydrogen phosphate, 4-(meth)acryloyloxyethyl trimellitate anhydride, 4-(meth)acryloyloxyethyl trimellitate, 2-(meth)acrylamide-2-methylpropanesulfonic acid, and 11-(meth)acryloyloxyundecane-1,1-dicarboxylic acid.

The content of the acid group-containing polymerizable monomer (a) is preferably 1 to 50 parts by mass, more preferably 2 to 30 parts by mass, and even more preferably 2 to 15 parts by mass in 100 parts by mass of the total polymerizable monomer components in the two-paste dental curable composition of the present invention. When the content of the acid group-containing polymerizable monomer (a) is 1 part by mass or more, high adhesiveness to various dental adherends is easily achieved. When the content of the acid group-containing polymerizable monomer (a) is 50 parts by mass or less, the balance between the polymerizability and adhesiveness is likely to be maintained. The term "total polymerizable monomer components in the two-paste dental curable composition" as used herein refers to the sum of the amounts of the acid group-containing polymerizable monomer (a), polymerizable monomer (b) having no acid group, later-described silane coupling agent (g), and later-described crosslinking agent (h) which are comprised in the first agent and/or a second agent (it should be noted that when a polymerizable group-containing silane coupling agent other than the silane coupling agent (g) is comprised in the two-paste dental curable composition, the total polymerizable monomer components includes the polymerizable group-containing silane coupling agent).

The polymerizable monomer (b) having no acid group is a polymerizable monomer that forms a polymer with advance of a radical polymerization reaction initiated by a polymerization initiator. In the two-paste dental curable composition of the present invention, both the first agent and second agent comprise the polymerizable monomer (b) having no acid group. The polymerizable monomer composing the polymerizable monomer (b) having no acid group of the present invention is not limited to one polymerizable monomer and may be two or more polymerizable monomers. Suitable examples of the polymerizable monomer (b) having no acid group include a water-soluble polymerizable monomer and hydrophobic polymerizable monomer described below.

The water-soluble polymerizable monomer refers to a polymerizable monomer having a solubility of 10 mass % or more in water at 25° C. The water-soluble polymerizable monomer preferably has a solubility of 30 mass % or more in water at 25° C., and is more preferably freely soluble in water at 25° C. The water-soluble polymerizable monomer promotes penetration of the other components of the two-paste dental curable composition into a tooth structure. The water-soluble polymerizable monomer itself also penetrates into a tooth structure and adheres to an organic component (collagen) in the tooth structure.

Examples of the water-soluble polymerizable monomer include 2-hydroxyethyl (meth)acrylate, 3-hydroxypropyl (meth)acrylate, 2-hydroxypropyl (meth)acrylate, 1,3-dihydroxypropyl (meth) acrylate, 2,3-dihydroxypropyl (meth)acrylate, 2-trimethylammoniummethyl (meth)acryl chloride, polyethylene glycol di(meth)acrylate (having 9 or more oxyethylene groups), and N-methacryloyloxyethyl acrylamide, and 2-hydroxyethyl (meth)acrylate is preferred.

The hydrophobic polymerizable monomer refers to a crosslinkable polymerizable monomer having a solubility of less than 10 mass % in water at 25° C. Examples of the crosslinkable polymerizable monomer include difunctional aromatic polymerizable monomers, difunctional aliphatic polymerizable monomers, and tri- or higher-functional polymerizable monomers. The hydrophobic polymerizable monomer improves the mechanical strength, handling properties, etc. of the two-paste dental curable composition.

Examples of the difunctional aromatic polymerizable monomer include an aromatic di(meth)acrylate represented by the following general formula [II]:

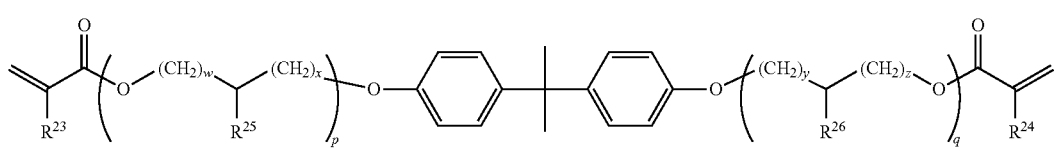

(In the formula, $R^{23}$ and $R^{24}$ are each a hydrogen atom or methyl group, $R^{25}$ and $R^{26}$ are each independently a hydrogen atom, hydroxy group, or alkyl group having 1 to 3 carbon atoms, w, x, y, and z are each an integer of 0 to 6, and p and q are each an integer of 0 to 8 and may be the same as or different from each other.) Specific examples of the difunctional aromatic polymerizable monomer include 2,2-bis((meth)acryloyloxyphenyl)propane, 2,2-bis[4-(3-acryloyloxy-2-hydroxypropoxy)phenyl]propane, 2,2-bis[4-(3-methacryloyloxy-2-hydroxypropoxy)phenyl]propane (which may hereinafter be simply referred to as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromellitate. Among these, 2,2-bis[4-(3-methacryloyloxy-2-hydroxypropoxy)phenyl]propane, 2,2-bis(4-methacryloyloxypolyethoxyphenyl)propane (having an average number of moles of added ethoxy groups of 2.6) (which may hereinafter be simply referred to as "D2.6E") are preferred.

Examples of the difunctional aliphatic polymerizable monomer include erythritol di(meth)acrylate, sorbitol di(meth)acrylate, mannitol di(meth)acrylate, pentaerythritol di(meth)acrylate, dipentaerythritol di(meth)acrylate, glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 2,2,4-trimethylhexamethylene bis(2-carbamoyloxyethyl) dimethacrylate, and 1,2-bis(3-methacryloyloxy-2-hydroxypropoxy)ethane. Among these, glycerol dimethacrylate, triethylene glycol di(meth)acrylate, neopentyl glycol dimethacrylate, 2,2,4-trimethylhexamethylene bis(2-carbamoyloxyethyl) dimethacrylate, and 1,2-bis(3-methacryloyloxy-2-hydroxypropoxy)ethane are preferred.

Examples of the tri- or higher-functional polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene)bis [2-(aminocarboxy)propane-1,3-diol] tetramethacrylate, and 1,7-diacryloyloxy-2,2,6,6-tetraacryloyloxymethyl-4-oxyheptane.

One of the above polymerizable monomers (b) having no acid group (the water-soluble polymerizable monomers and hydrophobic polymerizable monomers) may be added alone, or two or more thereof may be added in combination. The content of the polymerizable monomer (b) having no acid group is preferably 10 to 99 parts by mass and more preferably 50 to 95 parts by mass in 100 parts by mass of the total polymerizable monomer components in the two-paste dental curable composition of the present invention. The content of the water-soluble polymerizable monomer is preferably 1 to 50 parts by mass, more preferably 2 to 25 parts by mass, and even more preferably 3 to 10 parts by mass in 100 parts by mass of the total polymerizable monomer components in the two-paste dental curable composition of the present invention. The content of the hydrophobic polymerizable monomer is preferably 10 to 99 parts by mass and more preferably 50 to 95 parts by mass in 100 parts by mass of the total polymerizable monomer components in the two-paste dental curable composition.

When a mixture of two or more aromatic di(meth)acrylates each represented by the following general formula [II] is comprised in the two-paste dental curable composition (a mixture of the first agent and second agent) of the present invention as the polymerizable monomer (b) having no acid group, the ratio (mass ratio) between the contents of the mixture of two or more aromatic di(meth)acrylates each represented by the following general formula [II] and the silane coupling agent (g) is preferably 1:1 to 30:1, more preferably 3:1 to 25:1, and even more preferably 5:1 to 23:1 in view of the paste properties.

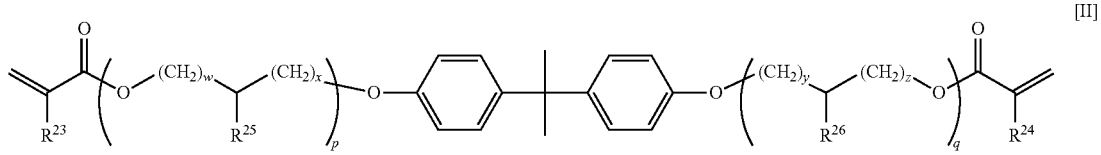

[II]

(In the formula, $R^{23}$, $R^{24}$, $R^{25}$, $R^{26}$, w, x, y, z, p, and q are as defined above.)

The first agent of the two-paste dental curable composition of the present invention comprises the polymerization initiator (c).

Examples of the polymerization initiator (c) include organic peroxides, inorganic peroxides, and transition metal complexes. Any commonly-known organic peroxides, inorganic peroxides, and transition metal complexes, exclusive of those mentioned as examples of the later-described photopolymerization initiator (j), can be used without limitation. One of the organic peroxides, inorganic peroxides, and transition metal complexes may be added alone, or two or more thereof may be added in combination.

Typical examples of the organic peroxide include hydroperoxides, peroxyesters, ketone peroxides, peroxyketals, dialkyl peroxides, diacyl peroxides, and peroxydicarbonates. Among these, hydroperoxides and peroxyesters are particularly preferred. Peroxyesters are most preferred because in that case, long-term storage of the two-paste dental curable composition of the present invention does not greatly change the time during which the two-paste dental curable composition can be handled. One of the organic peroxides may be used alone, or two or more thereof may be used in combination.

More specifically, examples of the hydroperoxide include cumene hydroperoxide, t-butyl hydroperoxide, t-hexyl hydroperoxide, p-menthane hydroperoxide, diisopropylbenzene hydroperoxide, and 1,1,3,3-tetramethylbutyl hydroperoxide (which may hereinafter be simply referred to as "THP").

Commonly-known peroxyesters can be used as the peroxyester without limitation as long as the commonly-known peroxyesters have an acyl group on one side of a peroxy group (—OO— group) and a hydrocarbon group (or a group similar thereto) on the other side of the peroxy group. Specific examples include α, α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3 -tetramethylbutylp eroxy-2-ethylhexanoate, 2,5-dimethyl-2,5-bis(2-ethylhexanoylperoxy)hexane, 1-cyclohexyl-1-methylethyl peroxy-2-ethylhexanoate, t-hexylperoxy-2 -ethylhexanoate, t-butyl peroxy-2-ethylhexanoate, t-butyl peroxyisobutyrate, t-hexylperoxyisopropyl monocarbonate, t-butyl peroxymaleic acid, t-butyl peroxy-3,5,5-trimethylhexanoate, t-butyl peroxylaurate, 2,5-dimethyl-2,5-bis(m-toluoyloxyperoxy)hexane, t-butylperoxyisopropyl monocarbonate, t-butylperoxy-2-ethylhexyl monocarbonate, t-hexyl peroxybenzoate, 2,5-dimethyl-2,5-bis(benzoylperoxy)hexane, t-butyl peroxyacetate, t-butyl peroxy-m-toluoylbenzoate, t-butyl peroxybenzoate (which may hereinafter be simply referred to as "BPB"), and bis(t-butylperoxy)isophthalate. One of these can be used alone, or two or more thereof can be used in appropriate combination. Among these, preferred are t-butyl peroxymaleic acid, t-butyl peroxy-3,5,5-trimethylhexanoate, t-butyl peroxybenzoate, t-butylperoxyisopropyl monocarbonate, t-butylperoxy-2-ethylhexyl monocarbonate, and t-butyl peroxyacetate and more preferred is t-butyl peroxybenzoate, in view of the storage stability and reactivity.

Examples of the ketone peroxide include methyl ethyl ketone peroxide, cyclohexanone peroxide, methylcyclohexanone peroxide, methyl acetoacetate peroxide, and acetylacetone peroxide.

Examples of the peroxyketal include 1,1-bis(t-hexylperoxy)3,3,5-trimethylcyclohexane, 1,1-bis(t-hexylperoxy)cyclohexane, 1,1-bis(t-butylperoxy)3,3,5-trimethylcydohexanone, 1,1-bis(t-butylperoxy)cyclohexane, 1,1-bis(t-butylperoxy)cyclodecane, 2,2-bis(t-butylperoxy)butane, n-butyl 4,4-bigt-butylperoxy)valerate, and 2,2-bis(4,4-di-t-butylperoxycyclohexyl)propane.

Examples of the dialkyl peroxide include α,α-bis(t-butylperoxy)diisopropylbenzene, dicumyl peroxide, 2,5-dimethyl-2,5-bis(t-butylperoxy)hexane, t-butyl cumyl peroxide, di-t-butyl peroxide, and 2,5-dimethyl-2,5-bis(t-butylperoxy)hexane-3.

Examples of the diacyl peroxide include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, and benzoyl peroxide.

Examples of the peroxydicarbonate include di-n-propylperoxydicarbonate, diisopropyl peroxy decarbonate, bis(4-t-butylcyclohexyl) peroxydicarbonate, di-2-ethoxyethyl peroxydicarbonate, di-2-ethylhexyl peroxydicarbonate, di-2-methoxybutyl peroxydicarbonate, and di(3-methyl-3-methoxybutyl) peroxydicarbonate.

Examples of the inorganic peroxide include peroxodisulfuric acid salts and peroxodiphosphoric acid salts. Among these, peroxodisulfuric acid salts are preferred in view of the curability. Specific examples of the peroxodisulfuric acid salt include sodium peroxodisulfate, potassium peroxodisulfate (which may hereinafter be simply referred to as "KPS"), aluminum peroxodisulfate, and ammonium peroxodisulfate.

In view of the curability, the content of the organic peroxide and that of the inorganic peroxide are each preferably 0.01 to 5 parts by mass and more preferably 0.05 to 2 parts by mass with respect to 100 parts by mass of the total polymerizable monomer components in the two-paste dental curable composition of the present invention.

Examples of the transition metal complex include copper compounds and vanadium compounds.

The copper compound is preferably a compound soluble in the polymerizable monomer components. Specific examples thereof include: as copper carboxylates, copper(II) acetate, copper(II) isobutyrate, copper(II) gluconate, copper (II) citrate, copper(II) phthalate, copper(II) tartrate, copper (II) oleate, copper(II) octylate, copper(II) octanoate, copper (II) naphthenate, copper(II) methacrylate, and copper(II) 4-cyclohexylbutyrate; as copper β-diketones, copper(II) acetylacetone, copper(II) trifluoroacetylacetone, copper(II) hexafluoroacetylacetone, 2,2,6,6-tetramethyl-3,5-heptanedionato copper(II), and copper(II) benzoylacetone; as copper β-ketoesters, copper(II) ethyl acetoacetate; as copper alkoxides, copper(II) methoxide, copper(II) ethoxide, copper(II) isopropoxide, copper(II) 2-(2-butoxyethoxy)ethoxide, and copper(II) 2-(2-methoxyethoxy)ethoxide; as copper dithiocarbamates, copper(II) dimethyklithiocarbamate; and as salts of copper and an inorganic acid, copper(II) nitrate and copper(II) chloride. One of these may be used alone, or two or more thereof may be used in appropriate combination. Among these, copper(II) carboxylates, copper(II) β-diketones, and copper(II) β-ketoesters are preferred and copper(II) acetate and copper(II) acetylacetone are particularly preferred, in view of the solubility in the polymerizable monomers and the reactivity with the polymerizable monomers.

In view of the curability, the content of the copper compound is preferably 0.000005 to 1 parts by mass with respect to 100 parts by mass of the total polymerizable monomer components in the two-paste dental curable composition of the present invention.

Examples of the vanadium compound include vanadium acetylacetonate, vanadyl acetylacetonate (which may hereinafter be simply referred to as "VOAA"), vanadyl stearate, vanadium naphthenate, and vanadium benzoylacetonate.

Vanadium acetylacetonate and vanadyl acetylacetonate are particularly preferred.

The content of the vanadium compound is preferably 0.005 to 1 parts by mass with respect to 100 parts by mass of the total polymerizable monomer components in the two-paste dental curable composition of the present invention in view of the curability.

The first agent of the two-paste dental curable composition of the present invention includes the filler (d).

Any fillers, inclusive of those mentioned as examples of the later-described filler (e) comprised in the second agent, can be used as the filler (d) as long as the effect of the present invention is not impaired. Examples of the filler (d) include inorganic fillers, organic fillers, and composite fillers formed of an inorganic filler and organic filler. One of the fillers (d) may be added alone, or two or more thereof may be added in combination. The filler (d) may not include the filler (e).

Examples of the inorganic filler include: silica; silica-based minerals, such as kaolin, clay, isinglass, and mica; and silica-based ceramics and glasses containing $Al_2O_3$, $B_2O_3$, $TiO_2$, $ZrO_2$, BaO, $La_2O_3$, SrO, ZnO, CaO, $P_2O_5$, $Li_2O$, $Na_2O$, etc. Examples of the glasses include lithium borosilicate glass, borosilicate glass, bio glass, lanthanum glass, barium glass, strontium glass, soda glass, zinc glass, and fluoroaluminosilicate glass. Crystalline quartz, hydroxyapatite, alumina, titanium oxide, yttrium oxide, zirconia, calcium phosphate, barium sulfate, aluminum hydroxide, sodium fluoride, potassium fluoride, sodium monofluorophosphate, lithium fluoride, and ytterbium fluoride are also suitably used as the inorganic fillers. Fine silica particles having an average particle diameter of 0.001 to 10 µm are preferably used in view of the bond strength and handling properties. Commercially-available inorganic fillers are, for example, "Aerosil (registered trademark) OX 50", "Aerosil (registered trademark) 50", "Aerosil (registered trademark) 200", "Aerosil (registered trademark) 380", "Aerosil (registered trademark) R972", and "Aerosil (registered trademark) 130" (these are names of products manufactured by Nippon Aerosil Co., Ltd.).

Examples of the organic filler include polymethyl methacrylate, polyethyl methacrylate, polymers of polyfunctional methacrylate, polyamide, polystyrene, polyvinyl chloride, chloroprene rubber, nitrile rubber, and styrene-butadiene rubber.

Examples of the composite filler formed of an inorganic filler and organic filler include: a composite filler obtained by dispersing an inorganic filler in an organic filler; and an inorganic-organic composite filler obtained by coating an inorganic filler with any of various polymers.

In the present specification, the average particle diameter of the filler (d) can be determined by a laser diffraction scattering method or by electron microscope observation of the particles. Specifically, the laser diffraction scattering method is convenient for particle diameter measurement on particles with a diameter of 0.1 µm or more, and electron microscope observation is convenient for particle diameter measurement on ultrafine particles with a diameter of less than 0.1 µm. 0.1 µm is a value determined by the laser diffraction scattering method.

To be specific about the laser diffraction scattering method, for example, the average particle diameter can be measured using a 0.2% aqueous solution of sodium hexametaphosphate as a dispersion medium by means of a laser diffraction particle size distribution analyzer (SALD-2100 manufactured by Shimadzu Corporation).

To be specific about the electron microscope observation, for example, the average particle diameter can be determined by taking a photograph of filler particles by means of a scanning electron microscope (S-4000 manufactured by Hitachi, Ltd.) and measuring the particle diameters of (200 or more) particles observed in a unit area of field of view in the photograph by the use of an image-analyzing particle size distribution analysis software (Mac-view (manufactured by Mountech Co., Ltd.)). In this case, the particle diameter of each particle is determined as an arithmetic mean of the maximum and minimum lengths of the particle, and, from the thus determined particle diameters and the number of the particles, the average particle diameter is calculated.

As the filler (d) used in the first agent, the inorganic fillers are preferred, and silica and the silica-based ceramics and glasses are more preferred.

In order to improve the curability, mechanical strength, and handling properties, the filler (d) may be surface-treated before use with a commonly-known surface treatment agent such as a silane coupling agent. Examples of the surface treatment agent include vinyltrimethoxysilane, vinyltriethoxysilane, vinyltrichlorosilane, vinyltri(β-methoxyethoxy)silane, γ-methacryloxypropyltrimethoxysilane, γ-glycidoxypropyltrimethoxysilane, γ-mercaptopropyltrimethoxysilane, and γ-aminopropyltriethoxysilane.

The second agent of the two-paste dental curable composition of the present invention comprises a polymerizable monomer (b) having no acid group, at least one filler (e) (suitably a basic filler (e1)) selected from the group consisting of a basic glass filler and alumina, a polymerization accelerator (f), and a silane coupling agent (g) represented by the following general formula [I]:

(In the formula, X represents a polymerizable functional group selected from the group consisting of a (meth)acryloxy group, a vinyl group, and an epoxy group, W represents a divalent aliphatic group optionally having a divalent group and having a linear chain having a carbon chain length of 5 or more or a divalent aromatic group optionally having a divalent group and having 6 or more carbon atoms, $R^2$, $R^3$, and $R^4$ are each independently a hydroxy group, an alkyl group having 1 to 5 carbon atoms, or an alkoxy group having 1 to 5 carbon atoms, and at least one of $R^2$, $R^3$, and $R^4$ is an alkoxy group having 1 to 5 carbon atoms.)

The polymerizable monomer (b) having no acid group is as described for the first agent.

Examples of the filler (e) include basic glass fillers such as lanthanum glass, barium glass, strontium glass, soda glass, zinc glass, and fluoroaluminosilicate glass and alumina. One of the fillers (e) may be added alone, or two or more thereof may be added in combination. Among these, barium glass and/or alumina is particularly suitably used in view of achieving high bond durability. The filler (e) is preferably the basic filler (e1) and is more preferably a basic glass filler. The pH of the basic filler (e1) is preferably 8.0 or more and 12.0 or less, more preferably 8.0 or more and 11.0 or less, and even more preferably 8.0 or more and 10.0 or less. An exemplary method for measuring the pH is a method in which 2 g of a filler is stirred in 50 ml of distilled water at about 20° C. and the pH of the mixture is measured 30 minutes later with a commonly-known pH meter (e.g., LAQUAact D-71AL manufactured by HORIBA, Ltd.). The addition of the filler (e) can inhibit hydrolysis of the alkoxy group of the silane coupling agent (g), inhibit the silane coupling agent (g) from undergoing a condensation reaction with the surface of the filler over time and being adsorbed onto the surface of the filler, and stabilize the silane coupling agent (g). This stabilization can prevent the amount of the silane coupling agent (g) adherable to lithium disilicate glass from gradually decreasing to lower the bond strength and can achieve high bond durability.

The filler (e) preferably has an average particle diameter of 0.001 to 10 µm in view of the bond strength and handling properties. The filler (e) is measured for the average particle diameter by a method same as that for the filler (d).

In order to improve the curability, mechanical strength, and handling properties, the filler (e) may be surface-treated before use with a commonly-known surface treatment agent such as a silane coupling agent. Examples of the surface treatment agent are the same as those mentioned as examples for the filler (d).

The sum of the contents of the filler (d) and filler (e) is preferably 10 to 80 mass %, more preferably 20 to 77 mass %, and most preferably 30 to 75 mass % with respect to the total mass of the two-paste dental curable composition of the present invention (the sum of the amounts of the first agent and second agent).

In the two-paste dental curable composition of the present invention, the second agent may further comprise a filler (k) different from the filler (e). As is the case for the filler (d), any fillers, exclusive of those falling under the filler (e), can be used as the filler (k) as long as the effect of the present invention is not impaired. The content of the filler (k) different from the filler (e) is preferably 30 parts by mass or less, more preferably 20 parts by mass or less, and even more preferably 10 parts by mass or less when the total filler components in the second agent is 100 parts by mass.

Examples of the polymerization accelerator (f) include aromatic amines, aliphatic amines, aromatic sulfinic acid salts, sulfur-containing reducing inorganic compounds, thiourea derivatives, benzotriazole compounds, and benzoimidazole compounds. One of the polymerization accelerators (f) may be used alone, or two or more thereof may be used in combination.

As the aromatic amine, commonly-known aromatic secondary amines and aromatic tertiary amines, etc. may be used. Examples of the aromatic secondary amine or aromatic tertiary amine include N,N-bis(2-hydroxyethyl)-3,5-dimethylaniline, N,N-bis(2-hydroxyethyl)-p-toluidine (which may hereinafter be simply referred to as "DEPT"), N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl) -4-t-butylaniline, N,N-bis (2-hydroxyethyl)-3,5-di-isopropylaniline, N,N-bis(2-hydroxyethyl)-3,5-di-ti-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. Among these, N,N-bis(2-hydroxyethyl)-p-toluidine is preferred in view of the redox reactivity.

Examples of the aliphatic amine include: primary aliphatic amines such as n-butylamine, n-hexylamine, and n-octylamine; secondary aliphatic amines such as diisopropylamine, dibutylamine, and N-methylethanolamine: tertiary aliphatic amines such as N-methylethanolamine, N-ethyldiethanolamine, N-n-butyldiethanolamine, N-lauryldiethanolamine, 2-(dimethylamino)ethyl (meth)acrylate, N-methyldiethanolamine di(meth)acrylate, N-ethyldiethanolamine di(meth)acrylate, triethanolamine tri(meth)acrylate, triethanolamine, trimethylamine, triethylamine, and tributylamine. Among these, tertiary aliphatic amines are preferred in view of the redox reactivity, and N-methyklethanolamine, triethanolamine, and 2-(dimethylamino)ethyl methacrylate are particularly preferred.

The content of the aromatic amine or aliphatic amine is preferably 0.01 to 10 parts by mass, more preferably 0.02 to 5 parts by mass, and even more preferably 0.05 to 2 parts by mass with respect to 100 parts by mass of the total polymerizable monomer components in the two-paste dental curable composition of the present invention. When the content of the aromatic amine or aliphatic amine is less than 0.01 parts by mass, the bond strength of the resultant two-paste dental curable composition to moist matter such as tooth structures may be lower. When the content of the aromatic amine or aliphatic amine is more than 10 parts by mass, the color stability of the resultant two-paste dental curable composition may be lower.

Examples of the aromatic sulfinic acid salt include lithium salts, sodium salts, potassium salts, rubidium salts, cesium salts, magnesium salts, calcium salts, strontium salts, iron salts, zinc salts, ammonium salts, tetramethylammonium salts, and tetraethylammonium salts of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid (a sodium salt thereof may hereinafter be simply referred to as "TPBSS"), chlorobenzenesulfinic acid, and naphthalenesulfinic acid. Among these, preferred are lithium salts, sodium salts, potassium salts, magnesium salts, and calcium salts of 2,4,6-trimethylbenzenesulfinic acid and 2,4,6-triisopropylbenzenesulfinic acid and more preferred are a lithium salt, sodium salt, potassium salt, magnesium salt, and calcium salt of 2,4,6-triisopropylbenzenesulfinic acid, in view of the curability and storage stability of the composition.

The content of the aromatic sulfinic acid salt is preferably 0.1 to 5 parts by mass, more preferably 0.2 to 4 parts by mass, and most preferably 0.5 to 3 parts by mass with respect to 100 parts by mass of the total polymerizable monomer components in the two-paste dental curable composition of the present invention. When the content of the aromatic sulfinic acid salt is less than 0.1 parts by mass or more than 5 parts by mass, the mechanical strength of a cured product of the resultant two-paste dental curable composition may be lower.

Examples of the sulfur-containing reducing inorganic compound include sulfurous acid salts, bisulfurous acid salts, pyrosulfurous acid salts, thiosulfuric acid salts, thionic acid salts, and dithionous acid salts. Among these, sulfurous acid salts and bisulfurous acid salts are preferred. Specific examples include sodium sulfite, potassium sulfite, calcium sulfite, ammonium sulfite, sodium hydrogen sulfite, and potassium hydrogen sulfite. One of the sulfur-containing reducing inorganic compounds may be used alone, or two or more thereof may be used in combination.

The content of the reducing inorganic compound is preferably 0.01 to 15 parts by mass, more preferably 0.05 to 10 parts by mass, and most preferably 0.1 to 5 parts by mass with respect to 100 parts by mass of the total polymerizable monomer components in the two-paste dental curable composition of the present invention. When the content of the reducing inorganic compound is less than 0.01 parts by mass, the bond strength of the resultant two-paste dental curable composition to moist matter such as tooth structures may be lower. When the content of the reducing inorganic compound is more than 15 parts by mass, the mechanical strength of a cured product of the resultant two-paste dental curable composition may be lower.

Examples of the thiourea derivative include ethylthiourea, dimethylethylenethiourea, N,N'-dimethylthiourea, N,N'-diethylthiourea, N,N'-di-n-propylthiourea, dicyclohexylthiourea, trimethylthiourea, triethylthiourea, tri-n-propylthiourea, tricyclohexylthiourea, tetramethylthiourea, tetraethylthiourea, tetra-n-propylthiourea, dicyclohexylthiourea, tetracyclohexylthiourea, N-acetylthiourea, N-benzoylthiourea, diphenylthiourea, and pyridylthiourea. Among these, 4,4-dimethylethylenethiourea, pyridylthiourea, and N-benzoylthiourea are preferred.

Examples of the benzotriazole compound and examples of the benzoimidazole compound respectively include a compound represented by the following general formula [III] and a compound represented by the following general formula [IV].

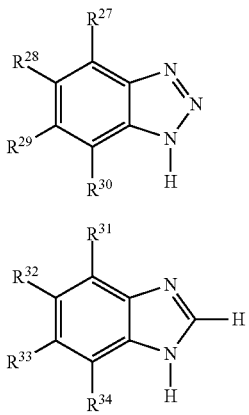

[III]

[IV]

In the above general formulae [III] and [IV], $R^{27}$ to $R^{34}$ each independently represent a hydrogen atom, hydroxy group, alkyl group, aryl group, alkoxy group, alkenyl group, aralkyl group, or halogen atom.

The alkyl group represented by $R^{27}$ to $R^{34}$ may be linear, branched, or cyclic and preferably has 1 to 10 carbon atoms. Specific examples thereof include a methyl group, ethyl group, n-propyl group, isopropyl group, cyclopropyl group, n-butyl group, isobutyl group, sec-butyl group, tert-butyl group, cyclobutyl group, n-pentyl group, isopentyl group, neopentyl group, tert-pentyl group, cyclopentyl group, n-hexyl group, isohexyl group, cyclohexyl group, n-heptyl group, cycloheptanyl group, n-octyl group, 2-ethylhexyl group, cyclooctyl group, n-nonyl group, cyclononyl group, and n-decyl group. Among these, a methyl group and ethyl group are particularly preferred.

The aryl group represented by $R^{27}$ to $R^{34}$ preferably has 6 to 10 carbon atoms. Examples thereof include a phenyl group, naphthyl group, and anthryl group.

The alkoxy group represented by $R^{27}$ to $R^{34}$ may be linear, branched, or cyclic and preferably has 1 to 8 carbon atoms. Specific examples thereof include a methoxy group, ethoxy group, n-propoxy group, isopropoxy group, n-butoxy group, tert-butoxy group, n-hexyloxy group, cyclohexyloxy group, n-octyloxy group, and 2-ethylhexyloxy group.

The alkenyl group represented by $R^{27}$ to $R^{34}$ may be linear, branched, or cyclic and preferably has 1 to 6 carbon atoms. Specific examples thereof include a vinyl group, allyl group, methylvinyl group, propenyl group, butenyl group, pentenyl group, hexenyl group, cyclopropenyl group, cyclobutenyl group, cyclopentenyl group, and cyclohexenyl group.

Examples of the aralkyl group represented by $R^{27}$ to $R^{34}$ include an alkyl group (particularly an alkyl group having 1 to 10 carbon atoms) substituted by an aryl group (particularly an aryl group having 6 to 10 carbon atoms). Specific examples thereof include a benzyl group.

Examples of the halogen atom represented by $R^{27}$ to $R^{34}$ include a chlorine atom, bromine atom, and iodine atom.

$R^{27}$ to $R^{34}$ are each preferably a hydrogen atom or methyl group.

One of the benzotriazole compounds and benzoimidazole compounds may be used alone, or two or more thereof may be used in combination. Specific examples of the benzotriazole compound and benzoimidazole compound include 1H-benzotriazole (which may hereinafter be simply referred to as "BTA"), 5-methyl-1H-benzotriazole, 5,6-dimethyl-1H-benzotriazole, benzoimidazole, 5-methylbenzoimidazole, and 5,6-dimethylbenzoimidazole. Among these, 1H-benzotriazole and 5-methyl-1H-benzotriazole are preferred in view of the color and storage stability of the composition.

X in the general formula [I] representing the silane coupling agent (g) represents a polymerizable functional group selected from the group consisting of a (meth)acryloxy group, vinyl group, and epoxy group, $R^1$ represents a divalent aliphatic group optionally having a divalent group and having a linear chain having a carbon chain length of 5 or more or a divalent aromatic group optionally having a divalent group and having 6 or more carbon atoms, $R^2$, $R^3$, and $R^4$ are each independently selected from the group consisting of a hydroxy group, an alkyl group having 1 to 5 carbon atoms, and an alkoxy group having 1 to 5 carbon atoms, and at least one of $R^2$, $R^3$, and $R^4$ is an alkoxy group having 1 to 5 carbon atoms. Examples of the divalent group include linking groups other than a carbon-carbon bond, such as an ether group, ester group, amide group, sulfonyl group, urethane group, and thioether group; and an alkylene group having 1 to 20 carbon atoms, alkenylene group having 2 to 20 carbon atoms, and alkynylene group having 2 to 20 carbon atoms. When $R^1$ is the aromatic group, the divalent group thereof is preferably an alkylene group. The number of carbon atoms of the alkylene group as the divalent group is preferably 1 to 15, more preferably) to 10, even more preferably 1 to 8, and particularly preferably 1 to 6. Examples of the alkylene group include a methylene group, ethylene group, n-propylene group, isopropylene group, trimethylene group, tetramethylene group, dimethylpropylene group, isobutylene group, pentamethylene group, hexamethylene group, heptamethylene group, octamethylene group, nonamethylene group, and decamethylene group. Furthermore, the divalent aliphatic group and divalent aromatic group may have a substituent. Examples of the substituent include: carbon atom-free substituents, such as a halogen atom, hydroxy group, oxo group, amino group, cyano group, and nitro group; and carbon atom-containing substituents, such as an alkyl group having 1 to 6 carbon atoms, alkoxy group having 1 to 6 carbon atoms, and alkenyl group having 2 to 6 carbon atoms. The number of substituents is preferably 1 to 10, more preferably 1 to 8, and even more preferably 1 to 4. The substituent of the aromatic group may be on an aromatic ring or may be on the alkylene group as the above divalent linking group.

The divalent aliphatic group represented by $R^1$ may be a divalent aliphatic group having a linear chain having a carbon chain length of 5 or more, and may have a branched chain as well as the linear chain. It is thought that thanks to the linear chain having a carbon chain length of 5 or more, molecules are easily arranged and hydrophobization of an adhesive interface can be promoted when a bond is formed on a silica-based ceramic (particularly lithium disilicate glass). As the above aliphatic group, an aliphatic group having a linear chain having a carbon chain length of 5 or more is preferred in view of further promoting the hydrophobization of the adhesive interface. The aliphatic group may consist of a carbon atom and hydrogen atom, or may contain a heteroatom such as an oxygen atom, nitrogen atom, or sulfur atom. The carbon chain length of the linear chain of the aliphatic group is preferably 6 or more, more preferably 7 or more, and even more preferably 8 or more. The carbon chain length of the linear chain of the aliphatic group is preferably 20 or less, more preferably 15 or less, and even more preferably 12 or less. Examples of the aliphatic group include an alkylene group, alkenylene group, and alkynylene group, and an alkylene group is preferred. Examples of the alkylene group include a dimethylpropylene group, pentamethylene group, hexamethylene group, heptamethylene group, octamethylene group, nonamethylene group, decamethylene group, undecamethylene group, and dodecamethylene group.

The divalent aromatic group represented by $R^1$ may be a homocyclic group containing a carbon atom only or may be a heterocyclic group. Examples of a heteroatom contained in the heterocyclic group include a nitrogen atom, sulfur atom, and oxygen atom. The number of heteroatoms contained in the heterocyclic group is preferably 1 to 3. The number of carbon atoms of the aromatic group optionally having a divalent group is preferably 6 to 35, more preferably 7 to 20, and even more preferably 8 to 16, inclusive of the number of carbon atoms contained in the divalent group. The preferred divalent aromatic group is an arylene group. Examples of the arylene group include: monocyclic aromatic groups such as a phenylene group, methylphenylene group (tolylene group), ethylphenylene group, dimethylphenylene group, trimethylphenylene group, diethylphenylene group, xylylene group, xylylene group, and xylylene group; and polycyclic aromatic groups such as a naphthylene group, anthracenylene group, phenanthrylene group, biphenylene group, and fluorenylene group. The aromatic group represented by $R^1$ is preferably an arylene group having an alkylene group. Two bonds of the aromatic group represented by $R^1$ may each be bonded to an alkylene group. Examples of the arylene group having an alkylene group include an ethylenephenylene group, diethylenephenylene group, triethylenephenylene group, propylenephenylene group, and butylenephenylene group. Additionally, the bonds of the divalent aromatic group are preferably located in para positions of an aromatic ring in view of further promoting the hydrophobization of an adhesive interface.

The number of carbon atoms of each alkyl group represented by $R^2$, $R^3$, or $R^4$ is preferably 1 to 3 and more preferably 1. The number of carbon atoms of each alkoxy group represented by $R^2$, $R^3$, or $R^4$ is preferably 1 to 3 and more preferably, in view of the bond durability to lithium disilicate glass, 1. Examples of the alkoxy group include a methoxy group, ethoxy group, n-propoxy group, isopropoxy group, n-butoxy group, sec-butoxy group, and tert-butoxy group. Examples of the alkyl group include a methyl group, ethyl group, n-propyl group, isopropyl group, n-butyl group, and isobutyl group. Each alkoxy group represented by $R^2$, $R^3$, or $R^4$ is more preferably a methoxy group in view of the bond durability to lithium disilicate glass.

With the use of the silane coupling agent (g), good bond durability to lithium disilicate glass can be achieved without using a primer. The reason is presumably that when an alkoxysilyl group is hydrolyzed to form a siloxane bond with a silanol group on the surface of a dental glass ceramic, particularly a lithium disilicate-containing glass ceramic, the adhesive interface is made sufficiently hydrophobic because of a long carbon chain between the (meth)acryloxy group and alkoxysilyl group and thus hydrolysis of the siloxane bond by water entry can be prevented.

One of the silane coupling agents (g) may be used alone, or two or more thereof may be used in combination. Any commonly-known silane coupling agents represented by the general formula [I] can be used as the silane coupling agent (g) without limitation. Specific examples include 5-(meth)acryloxypentyltrimethoxysilane, 6-(meth)acryloxyhexyltrimethoxysilane, 7-(meth)acryloxyheptyltrimethoxysilane, 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, 8-(meth)acryloxyoctylmethyldimethoxysilane, 10-(meth)acryloxydecylmethyldimethoxysilane, 11-(meth)acryloxyundecylmethyldimethoxysilane, and (meth)acryloxymethylphenethyltrimethoxysilane.

Among these silane coupling agents (g), 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, and (meth)acryloxymethylphenethyltrimethoxysilane are suitably used particularly in view of the bond durability to lithium disilicate glass and the handling properties.

With respect to the total mass of the two-paste dental curable composition of the present invention, the content of the silane coupling agent (g) is preferably 0.1 to 10.0 mass% in view of excellent bond strength. The content of the silane coupling agent (g) is more preferably 0.5 to 9.0 mass %, even more preferably 1.0 to 8.0 mass %, and particularly preferably 1.2 to 7.0 mass % in view of the bond durability to lithium disilicate glass.

The crosslinking agent (h) comprises a compound represented by the following general formula [V]:

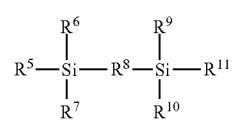

and/or a compound represented by the general formula [VI]:

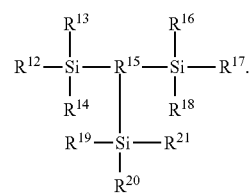

(In the formulae, $R^8$ represents a divalent aliphatic group optionally having a divalent group and having a carbon chain length of 1 or more or a divalent aromatic group optionally having a divalent group and having 6 or more carbon atoms, $R^{15}$ represents a trivalent aliphatic group having a carbon chain length of 1 or more or a trivalent aromatic group optionally having a divalent group and having 6 or more carbon atoms, and $R^5$ to $R^7$, $R^9$ to $R^{14}$, and $R^{16}$ to $R^{21}$ each independently represent a hydroxy group or an alkoxy group having 1 to 5 carbon atoms.)

$R^8$ in the general formula [V] is preferably a divalent aliphatic group optionally having a divalent group and having a carbon chain length of 1 to 10 or a divalent aromatic group optionally having a divalent group and having 6 to 10 carbon atoms. $R^{15}$ in the general formula [VI] is preferably a trivalent aliphatic group having a carbon chain length of 1 to 10 or a trivalent aromatic group optionally having a divalent group and having 6 to 10 carbon atoms. The aliphatic group and aromatic group represented by $R^8$ and $R^{15}$ may consist of a carbon atom and hydrogen atom, or may contain an oxygen atom, sulfur atom, or nitrogen atom. Examples of the above divalent groups are the same as those described as examples of the divalent group in $R^1$. Moreover, the divalent aliphatic group and divalent aromatic group may have a substituent. Examples of the substituent are the same as those described as examples of the substituent in $R^1$. The substituent of the above aromatic groups may be on an aromatic ring or may be on the alkylene group as the above divalent linking group.

The aliphatic group and aromatic group represented by $R^8$ and $R^{15}$ each may be a homocyclic group containing a carbon atom only, or may be a heterocyclic group. Examples of a heteroatom contained in the heterocyclic group include a nitrogen atom, sulfur atom, and oxygen atom. The number of heteroatoms contained in the heterocyclic group is preferably 1 to 3. Examples of the heterocyclic groups represented by $R^8$ and $R^{15}$ include one-heteroatom-containing six-membered heterocyclic groups such as a pyran ring and pyridine ring; two-heteroatom-containing six-membered heterocyclic groups such as a pyridazine ring, pyrazine ring, and pyrimidine ring; and three-heteroatom-containing six-membered heterocyclic groups such as triazine rings (1,2,3-triazine ring, 1,2,4-triazine ring, and 1,3,5-triazine ring). Examples of the heterocyclic group include an isocyanuric acid group. In an embodiment, each aromatic group represented by $R^8$ or $R^{15}$ is preferably a heterocyclic group, more preferably a two-heteroatom-containing six-membered heterocyclic group or a three-heteroatom-containing six-membered heterocyclic group, and even more preferably a three-heteroatom-containing six-membered heterocyclic group. In another embodiment, the crosslinking agent (h) is preferably a compound represented by the general formula [V], in which $R^8$ is preferably a divalent aliphatic group optionally having a divalent group and having 1 or more carbon atoms.

The divalent aliphatic group represented by $R^8$ and having a carbon chain length of 1 to 10 may be linear, branched, or cyclic. The number of carbon atoms of the divalent aliphatic group is preferably 2 or more and more preferably 3 or more.

Examples of the aliphatic group include an alkylene group having 1 to 10 carbon atoms, alkenylene group having 2 to 10 carbon atoms, alkynylene group having 2 to 10 carbon atoms, cycloalkylene group having 3 to 10 carbon atoms, and an alkylene group is preferred. Examples of the alkylene group include a methylene group, ethylene group, n-propylene group, isopropylene group, trimethylene group, tetramethylene group, dimethylpropylene group, isobutylene group, pentamethylene group, hexamethylene group, heptamethylene group, octamethylene group, nonamethylene group, and decamethylene group. Examples of the divalent aromatic group represented by $R^8$ are the same as those mentioned as examples of the divalent aromatic group represented by $R^1$.

The trivalent aliphatic group represented by $R^{15}$ and having a carbon chain length of 1 to 10 may be linear or branched. The number of carbon atoms of the trivalent aliphatic group is preferably 2 to 9 and more preferably 3 to 8. Examples of the trivalent aliphatic group include groups that are the same as those mentioned as examples of the divalent aliphatic group represented by $R^8$ except that one hydrogen atom is removed therefrom. The number of carbon atoms of the trivalent aromatic group represented by $R^{15}$ is preferably 6 to 35, more preferably 7 to 20, and even more preferably 8 to 16. Examples of the trivalent aromatic group include groups that are the same as those mentioned as examples of the divalent aromatic group represented by $R^8$ except that one hydrogen atom is removed therefrom.

$R^5$ to $R^7$, $R^9$ to $R^{14}$, and $R^{16}$ to $R^{21}$ each independently represent a hydroxy group or an alkoxy group having 1 to 5 carbon atoms. The alkoxy group may be linear or branched. Examples of the alkoxy group include a methoxy group, ethoxy group, n-propoxy group, isopropoxy group, n-butoxy group, sec-butoxy group, and tert-butoxy group, and a methoxy group and ethoxy group are most preferred.

It is thought that an alkoxysilyl group of the crosslinking agent (h) and the alkoxysilyl group of the silane coupling agent (g) separately undergo hydrolysis and then a condensation reaction to form a siloxane bond, which provides the silane coupling agent (g) with a lot of reactive sites between the silane coupling agent (g) and the surface of lithium disilicate glass to allow achievement of better bond durability.

Preferred examples of the crosslinking agent (h) include 1,2-bis(triethoxysilyl)ethane (which may hereinafter be simply referred to as "BSE"), 1,4-bis(triethoxysilyl)benzene (which may hereinafter be simply referred to as "BSB"), 1,4-bis(triethoxysilylethyl)benzene, 4,4'-bis(triethoxysilyl)-1,1'-biphenyl, 1,8-bis(triethoxysilyl)octane, 1,2-bis(trimethoxysilyl)decane, 1,6-bis(triethoxysilyl)hexane (which may hereinafter be simply referred to as "BSH"), 1,6-bis(trimethoxysilyl)-2,5-dimethylhexane, 1,4-bis(trimethoxysilylethyl)benzene, 1,6-bis(trimethoxysilyl)hexane, 1,4-bis(trimethoxysilylmethyl)benzene, 1,8-bis(trimethoxysilyl)octane (which may hereinafter be simply referred to as "BSO"), tris(trimethoxysilylpropyl)isocyanurate (which may hereinafter be simply referred to as "TSPI"), and N,N-bis[3-(trimethoxysilyl)propyl] amine. Among these, 1,4-bis(triethoxysilyl)benzene and tris(trimethoxysilylpropyl)isocyanurate are most preferred. One of the crosslinking agents (h) may be used alone, or two or more thereof may be used in combination.

The content of the crosslinking agent (h) is preferably 0.05 to 10.0 mass %, more preferably 0.1 to 5.0 mass %, and even more preferably 0.2 to 3.0 mass % with respect to the total mass of the two-paste dental curable composition in view of excellent bond durability A silanol condensation catalyst (i) is a compound represented by the following general formula [VII].

$$M(R^{22})_n \qquad [VII]$$

(In the formula, M represents Ti, Zr, or Al, $R^{22}$ represents an aliphatic group, n represents an integer of 1 to 4, and when there are two or more $R^{22}$, the two or more R22 may be the same as or different from each other.)

The silanol condensation catalyst (i) is thought to promote condensation not only between alkoxysilanes but also between an alkoxysilane and the surface of a silica-based ceramic. With the use of the silanol condensation catalyst (i), a reaction with the surface of a silica-based ceramic (particularly lithium disilicate glass) is reliably carried out to improve the bond durability.

The aliphatic group represented by $R^{22}$ may consist of a carbon atom and hydrogen atom, or may contain one or more oxygen atoms, one or more sulfur atoms, or one or more NH group, and preferably contains one or more oxygen atom. The aliphatic group represented by $R^{22}$ may have an unsaturated bond. The number of carbon atoms of the aliphatic group represented by $R^{22}$ is preferably 1 to 20, more preferably 1 to 16, and even more preferably 1 to 10. Moreover, the aliphatic group represented by $R^{22}$ may have a substituent. Examples of the substituent are the same as those described as examples of the aliphatic group represented by $R^1$. Examples of the aliphatic group represented by $R^{22}$ include an alkoxy group having 1 to 9 carbon atoms, an acyloxy group having 2 to 9 carbon atoms, an alkenyloxy group having 3 to 9 carbon atoms, a 6-diketonate group having 5 to 15 carbon atoms, and a diacylmethyl group having acyl groups each having 1 to 9 carbon atoms.

Examples of the alkoxy group include a methoxy group, ethoxy group, n-propoxy group, isopropoxy group, n-butoxy group, isobutoxy group, sec-butoxy group, tert-butoxy group, benzyloxy group, diphenylmethoxy group, trityloxy group, 4-methoxybenzyloxy group, methoxymethoxy group, 1-ethoxyethoxy group, benzyloxymethoxy group, 2-trimethylsilylethoxy group, 2-trimethylsilylethoxymethoxy group, phenoxy group, and 4-methoxyphenoxy group. Examples of the acyloxy group include an acetoxy group, ethylcarbonyloxy group, n-propylcarbonyloxy group, isopropylcarbonyloxy group, n-butylcarbonyloxy group, isobutylcarbonyloxy group, sec-butylcarbonyloxy group, tert-butylcarbonyloxy group, and n-octylcarbonyloxy group. Examples of the alkenyloxy group include an allyloxy group, 2-propenyloxy group, 2-butenyloxy group, 1-methyl-2-propenyloxy group, 3-butenyloxy group, 2-methyl-2-propenyloxy group, 2-pentenyloxy group, 3-pentenyloxy group, 4-pentenyloxy group, 1-methyl-3-butenyloxy group, 1,2-dimethyl-2-propenyloxy group, 1,1-dimethyl-2-propenyloxy group, 2-methyl-2-butenyloxy group, 3-methyl-2-butenyloxy group, 2-methyl-3-butenyloxy group, 3-methyl-3-butenyloxy group, 1-vinyl-2-propenyloxy group, and 5-hexenyloxy group. Examples of the β-diketonate group include an —O—C(CH$_3$)=CH—C (=O)—CH$_3$) group (acetylacetonate group), (—O—C (CH$_3$)=CH—C(=O)—CH$_2$—CH$_3$) group (propionylacetonate group), 2,2,6,6-tetramethyl-3,5-heptanedionate group, 1,3-butanedionate group, and 2-methyl-1,3-butaneclionate group. Examples of the acyl group of the diacylmethyl group include: aliphatic acyl groups having 1 to 6 carbon atoms, such as a formyl group, acetyl group, propionyl group (propanoyl group), butyryl group (butanoyl group), valeryl group (pentanoyl group), and hexanoyl group; and aromatic acyl groups (aroyl groups), such as a benzoyl group and toluoyl group.

The symbol n in the general formula [VII] is preferably 3 or 4 depending on the type of the metal represented by M. For example, when M is titanium(IV) or zirconium(IV), n is preferably 4. When M is zirconium(III), n is preferably 3.

Specific examples of the silanol condensation catalyst (i) include metal-based catalysts such as: titanium esters such as titanium(IV) tetrabutoxide and titanium(IV) tetrapropoxide; organic aluminum compounds such as aluminum(III) acetylacetonate, aluminum trisethylacetoacetate, and diisopropoxyaluminum ethylacetoacetate; and chelate compounds such as zirconium(IV) tetraacetylacetonate, titanium (IV) acetylacetonate, titanium(IV) bis(acetylacetonate) cliisopropoxide, titanium(IV) bis(ethyl aceto acetate) diisopropoxide, and titanium(IV) bis(ethylhexoxy) bis(2-ethyl-3-hydroxyhexoxide). One of these metal-based catalysts may be used alone, or two or more thereof may be used in combination.

The content of the silanol condensation catalyst (i) is preferably 0.001 to 10.0 mass %, more preferably 0.01 to 5.0 mass %, and even more preferably 0.1 to 3.0 mass % with respect to the total mass of the two-paste dental curable composition in view of excellent bond durability.

In addition to the polymerization initiator (c), a conventionally known photopolymerization initiator (j) may be further added to at least one of the first agent and second agent so that the two-paste dental curable composition of the present invention is of a dual-cure type whose polymerization is initiated upon irradiation with light. Examples of the photopolymerization initiator (j) include α-diketones, ketals, thioxanthones, (bis)acylphosphine oxides, and α-aminoacetophenones.

Examples of the α-diketone include camphorquinone (commonly known as "CQ"), benzyl, and 2, 3-pentanedione.

Examples of the ketal include benzyl dimethyl ketal and benzyl diethyl ketal.

Examples of the thioxanthone include 2-chlorothioxanthone and 2,4-diethylthioxantone.

Examples of the (bis)acylphosphine oxides include 2,4, 6-trimethylbenzoyl diphenylphosphine oxide, bis(2,4,6-trimethylbenzoyl)phenylphosphine oxide, dibenzoylphenylphosphine oxide, bis(2,6-dimethoxybenzoyl) phenylphosphine oxide, tris(2,4-dimethylbenzoyl) phosphine oxide, tris(2-methoxybenzoyl)phosphine oxide, 2,6-dimethoxybenzoykliphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphine oxide, 2,4,6-trimethylbenzoylethoxyphenylphosphine oxide, and the water-soluble acylphosphine oxide compound disclosed in JP H03-057916 B2.

Examples of the α-aminoacetophenone include 2-benzyl-2-dimethylamino-1-(4-morpholinophenyl)-1-butanone, 2-benzyl-2-diethylamino-1-(4-morpholinophenyl)-1-butanone, 2-benzyl-2-dimethylamino-1-(4-morpholinophenyl)-1-propanone, 2-benzyl-2-diethylamino-1-(4-morpholinophenyl)-1-propanone, 2-benzyl-2-dimethylamino-1-(4-morpholinophenyl)-1-pentanone, and 2-benzyl-2-diethylamino-1-(4-morpholinophenyl) -1-pentanone.

One of the photopolymerization initiators (j) may be used alone, or two or more thereof may be used in combination. The content of the photopolymerization initiator (j) is preferably 0.005 to 10 parts by mass and more preferably 0.01 to 5 parts by mass with respect to 100 parts by mass of the total polymerizable monomer components in the two-paste dental curable composition of the present invention.

Additionally, the photopolymerization initiator (j) and a polymerization accelerator, examples of which include aldehydes, thiol compounds, and triazine compounds substituted by a trihalomethyl group, may be used in combination to enhance the photocurability. Examples of the aldehydes include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde. Examples of the thiol compounds include 3-mercaptopropyltrimethoxysilane, 2-mercaptobenzoxazole, decanethiol, and thiobenzoic acid. One of these polymerization accelerators may be used alone, or two or more thereof may be used in combination. Any commonly-known compounds can be used as the triazine compound substituted by a trihalomethyl group without limitation as long as the commonly-known compounds are s-triazine compounds having at least one trihalomethyl group such as a trichloromethyl group or tribromomethyl group.

One of the triazine compounds may be used alone, or two or more thereof may be used in combination, if needed. The content of the triazine compound is 0.005 to 0.3 parts by mass, preferably 0.008 to 0.2 parts by mass, and more preferably 0.01 to 0.1 parts by mass with respect to 100 parts by mass of the total polymerizable monomer components in the two-paste dental curable composition of the present invention.

A fluorine ion-releasing material may be added to the two-paste dental curable composition of the present invention in order to impart the acid resistance to tooth structures. Examples of the fluorine ion-releasing material include: fluorine ion-releasing polymers such as a copolymer of methyl methacrylate and methacryloyl fluoride; fluorine ion-releasing materials such as cetylamine hydrofluoride; and inorganic fillers such as fluoroaluminosilicate glass, sodium fluoride, potassium fluoride, sodium monofluorophosphate, lithium fluoride, and ytterbium fluoride.

An additive such as a stabilizer (polymerization inhibitor), colorant, fluorescent agent, or ultraviolet absorber may be added to the two-paste dental curable composition of the present invention. Moreover, an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, or triclosan may be added.

A commonly-known dye or pigment may be added to the two-paste dental curable composition of the present invention.

The first agent of the present invention may consist essentially of the polymerizable monomer (a) having an acid group, polymerizable monomer (b) having no acid group, polymerization initiator (c), and filler (d). Likewise, the second agent of the present invention may consist essentially of the polymerizable monomer (b) having no acid group, filler (e) (suitably the basic filler (e1)), polymerization accelerator (f), and silane coupling agent (g) represented by the general formula [I]. Saying that a material "consists essentially of a certain component(s)" means that components other than the certain component(s) are not included essentially. Therefore, for example, the total content of the components other than the certain component(s) is preferably less than 5.0 mass %, more preferably less than 1.0 mass %, even more preferably less than 0.5 mass %, and particularly preferably less than 0.1 mass %.

The two-paste dental curable composition of the present invention can be produced, for example, by mixing the components other than the powder components (the filler (d), filler (e), etc.) to obtain a solution, to which the powder components are added.

The present invention encompasses embodiments obtainable by combining the above features in various manners within the technical scope of the present invention as long as the effect of the present invention can be obtained.

EXAMPLES

Hereinafter, the present invention will be described in more detail by way of examples. It should be noted that the present invention is not limited by any means by the following examples and many modifications can be made by those having ordinary skill in the art within the technical scope of the present invention.

Abbreviations used hereinafter are as follows.

Acid Group-Containing Polymerizable Monomer (a)

MDP: 10-methacryloyloxydecyl dihydrogen phosphate

Polymerizable Monomer (b) Having No Acid Group

HEMA: 2-hydroxyethyl methacrylate
Bis-GMA: 2,2-bis[4-(3-methacryloyloxy-2-hydroxypropoxy)phenyl]propane
D2ME: 2,2-bis(4-methacryloyloxypolyethoxyphenyl)propane (having an average number of moles of added ethoxy groups of 2.6)

Polymerization Initiator (c)

Copper(II) acetate
VOAA: vanadyl acetylacetonate
BPB: t-butyl peroxybenzoate
BPO: benzoyl peroxide
KPS: potassium persulfate
THP: 1,1,3,3-tetramethylbutyl hydroperoxide Filler (d)

F1: Silane-treated quartz powder:
Quartz (manufactured by MARUWA QUARTZ CO., LTD.) was ground in a ball mill to obtain a quartz powder having an average particle diameter of about 4.5 μm. By a conventional method, 100 parts by mass of this quartz powder was surface-treated with 3 parts by mass of γ-methacryloxypropyltrimethoxysilane to obtain a silane-treated quartz powder.
R972: Fine silica particles "Aerosil (registered trademark) R972" manufactured by Nippon Aerosil Co., Ltd. and having an average particle diameter of 16 nm Filler (e)

F2: Silane-treated barium glass powder:
Barium glass (product code "Raysorb E-3000" manufactured by Esstech, Inc.) was ground in a ball mill to obtain a barium glass powder having an average particle diameter of about 2.4 μm. By a conventional method, 100 parts by mass of this barium glass powder was surface-treated with 3 parts by mass of γ-methacryloxypropyltrimethoxysilane to obtain a silane-treated barium glass powder.
Alumina: Product name "AEROXIDE Alu C", manufactured by Nippon Aerosil Co., Ltd. and having an average particle diameter of 13 nm and a pH of 4.5 to 5.5

Polymerization Accelerator (f)

TPBSS: sodium 2,4,6-trIisopropylbenzenesulfinate
DEPT: N,N-bis(2-hydroxyethyl)-p-toluidine
BTA: 1H-benzotriazole
DME TU: 4,4-dimethylethylenethiourea Silane Coupling Agent (g)

8-MOS: 8-methacryloxyoctyltrimethoxysilane
11-MUS: 11-methacryloxyundecyltrimethoxysilane
11-MUE S: 11-methacryloxyundecyltriethoxysilane
APhS: acryloxymethylphenethyltrimethoxysilane

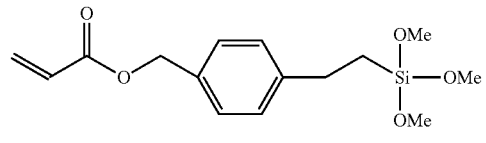

APhS

Other Silane Coupling Agents

γ-MPS γ-methacryloxypropyltrimethoxysilane
γ-MPES: γ-methacryloxypropyltriethoxysilane Crosslinking Agent (h)

TSPI: tris(trimethoxysilylpropyl)isocyanurate
BSB: 1,4-bis(triethoxysilyl)benzene
BSE: 1,2-bis(triethoxysilyl)ethane
BSH: 1,6-bigtriethoxysilyl)hexane
BSO: 1,8-bis(trimethoxysilyl)octane Silanol Condensation Catalyst (i)

Ti(OBu)$_4$: titanium(IV) tetrabutoxide
Ti(C$_3$H$_7$O)$_2$(AcAc)$_2$: titanium(IV) bis(acetylacetonate) diisopropoxide (75% isopropanol solution)
Ti(C$_3$H$_7$O)$_2$(C$_6$H$_9$O$_3$)$_2$: titanium(IV) bis(ethylacetoacetate)diisopropoxide (95% isopropanol solution)
Ti(C$_8$H$_{17}$O)$_2$(C$_8$H$_{17}$O$_2$)$_2$: titanium(IV) bis (ethylhexoxy) bis (2-ethyl-3-hydroxyhexoxide)
Zr(C$_5$H$_7$O$_2$)$_4$: zirconium(IV) tetraacetylacetonate Photopolymerization initiator (j)

CQ: dl-camphorquinone

Others

PDE: 4-(N,N-dimethylamino)ethyl benzoate (polymerization accelerator for the photopolymerization initiator)
BHT: 2,6-di-t-butyl-4-methylphenol (stabilizer)

Examples 1 to 17 and Comparative Examples 1 and 2

First agents and second agents having the compositions shown in Table 1 and Table 2 were prepared. Each of the first agents was produced by preparing the components other than the powder component (fillers), stirring the components to obtain a homogeneous solution, kneading the powder component into the homogeneous solution, and then defoaming the resultant mixture. The powder component in the first agent was dispersed in the form of a powder. Each of the second agents was produced by preparing the components other than the powder components (fillers and TPBSS), stirring the components to obtain a homogeneous solution, kneading the powder components into the homogeneous solution, and then defoaming the resultant mixture. The powder components in the second agent were dispersed in the form of a powder. The two agents were separately loaded into a double syringe (a 5 mL double syringe manufactured by Sulzer Mixpac AG), and a plunger was set. A mixing tip (manufactured by Sulzer Mixpac AG) was attached to the end of the double syringe. The two agents were automatically mixed at a mass ratio of 1:1, and the mixture was used as a dental curable composition in evaluation. The tensile bond strength to porcelain and lithium disilicate glass was tested by the following methods. The results are shown in Table 1 and Table 2.

Tensile Bond Strength to Porcelain

A dental porcelain (feldspar ceramic "VITABLOCS Mark II" manufactured by VITA Zahnfabrik H. Rauter GmbH & Co. KG) was ground with #1000 silicon carbide paper under running water. After the grinding, the dental porcelain was dried by removing water from its surface by air-blowing. To the dried smooth surface was attached an about 150-µm-thick adhesive tape having a circular hole of 5-mm diameter, so that an adhesive area was delimited The dental curable composition obtained by mixing the first agent and second agent in each of Examples and Comparative Examples was mounded to one end face (circular end face) of a cylindrical stainless steel rod (with a diameter of 7 mm and a length of 2.5 cm). Then, the end face with the dental curable composition mounded thereon was placed on the smooth surface (adherend) within the circular hole in such a manner that the center of the circular hole and the center of the cylindrical stainless steel rod substantially coincided with each other. The cylindrical stainless steel rod was perpendicularly pressed against and bonded to the smooth surface, and thus a test sample was prepared. There were prepared 10 such test samples. An excess portion of the dental curable composition that spread out of the perimeter of the cylindrical stainless steel rod during the pressing was removed. Then the test samples were allowed to stand at room temperature for 30 minutes and immersed in distilled water. The test samples immersed in distilled water were allowed to stand in a thermostat maintained at 37° C. for 24 hours. Five out of the 10 test samples were examined for the tensile bond strength after allowed to stand at 37° C. for 24 hours. The tensile bond strength thus examined represents the initial tensile bond strength. The remaining 5 test samples were examined for the tensile bond strength after further allowed to stand in a thermostat maintained at 70° C. for 10 days. The tensile bond strength thus examined represents the bond durability. The tensile bond strength was measured using a universal testing machine (manufactured by Shimadzu Corporation) with the crosshead speed set to 2 mm/min. Each tensile bond strength value shown in the tables is an average of values measured for the 5 test samples allowed to stand at 37° C. for 24 hours or an average of values measured for the 5 test samples allowed to stand at 70° C. for 10 days.

Tensile Bond Strength to Lithium Disilicate Glass Ceramic

A dental lithium disilicate glass ceramic ("IPS e.max CAD" manufactured by Ivoclar Vivadent AG) was sintered according to the conditions of a sintering program described in its product literature and was then ground with #1000 silicon carbide paper under running water. After the grinding, the dental lithium disilicate glass ceramic was dried by removing water from its surface by air-blowing. To the dried smooth surface was attached an about 150-µm-thick adhesive tape having a circular hole of 5-mm diameter, so that an adhesive area was defined. The dental curable composition obtained by mixing the first agent and second agent in each of Examples and Comparative Examples was mounded to one end face (circular end face) of a cylindrical stainless steel rod (with a diameter of 7 mm and a length of 2.5 cm). Then, the end face with the dental curable composition mounded thereon was placed on the smooth surface (adherend) within the circular hole in such a manner that the center of the circular hole and the center of the cylindrical stainless steel rod substantially coincided with each other. The cylindrical stainless steel rod was perpendicularly pressed against and bonded to the smooth surface, and thus a test sample was prepared. There were prepared 10 such test samples. An excess portion of the dental curable composition that spread out of the perimeter of the cylindrical stainless steel rod during the pressing was removed.

Then the test samples were allowed to stand at room temperature for 30 minutes and immersed in distilled water. The test samples immersed in distilled water were allowed to stand in a thermostat maintained at 37° C. for 24 hours. Five out of the 10 test samples were examined for the tensile bond strength after allowed to stand at 37° C. for 24 hours. The tensile bond strength thus examined represents the initial tensile bond strength. The remaining 5 test samples were examined for the tensile bond strength after further allowed to stand in a thermostat maintained at 70° C. for 3 days. The tensile bond strength thus examined represents the bond durability. The tensile bond strength was measured using a universal testing machine (manufactured by Shimadzu Corporation) with the crosshead speed set to 2 mm/min. Each tensile bond strength value shown in the tables is an average of values measured for the 5 test samples allowed to stand at 37° C. for 24 hours or an average of values measured for the 5 test samples allowed to stand at 70° C. for 3 days.

TABLE 1

| | | | Example 1 | Example 2 | Example 3 | Example 4 | Example 5 | Example 6 | Example 7 | Example 8 | Example 9 |
|---|---|---|---|---|---|---|---|---|---|---|---|
| First agent | Polymerizable monomer (a) having an acid group | MDP | 20 | 20 | 20 | 20 | 20 | 20 | 20 | 20 | 20 |
| | Polymerizable monomer (b) having no acid group | Bis-GMA | 40 | 40 | 40 | 40 | 40 | 40 | 40 | 40 | 40 |
| | | D2.6E | 25 | 25 | 25 | 25 | 25 | 25 | 25 | 25 | 25 |
| | | HEMA | 15 | 15 | 15 | 15 | 15 | 15 | 15 | 15 | 15 |
| | Polymerization initiator (c) | Copper(II) acetate | 0.001 | 0.001 | 0.001 | 0.001 | 0.001 | 0.001 | 0.001 | 0.001 | 0.001 |
| | | VOAA | | | | | | | | | |
| | | BPB | 0.5 | 0.5 | 0.5 | 0.5 | 0.5 | 0.5 | 0.5 | 0.5 | 0.5 |
| | | BPO | | | | | | | | | |
| | | KPS | | | | | | | | | |
| | | THP | | | | | | | | | |
| | Filler (d) | F1 (silica) | 215 | 215 | 215 | 215 | 215 | 215 | 215 | 215 | 215 |
| | | R972 | 15 | 15 | 15 | 15 | 15 | 15 | 15 | 15 | 15 |
| | Silanol condensation catalyst (i) | Ti(OBu)$_4$ | | | | | | | | | 1 |
| | | Ti(C$_3$H$_7$O)$_2$(AcAc)$_2$ | | | | | | | | | |
| | | Ti(C$_3$H$_7$O)$_2$(C$_6$H$_9$O$_3$)$_2$ | | | | | | | | | |
| | | Ti(C$_8$H$_{17}$O)$_2$(C$_8$H$_{17}$O$_2$)$_2$ | | | | | | | | | |
| | | Zr(C$_5$H$_7$O$_2$)$_4$ | | | | | | | | | |
| | Photopolymerization initiator (j) | CQ | 0.1 | 0.1 | 0.1 | 0.1 | 0.1 | 0.1 | 0.1 | 0.1 | 0.1 |
| | Other | BHT | 0.15 | 0.15 | 0.15 | 0.15 | 0.15 | 0.15 | 0.15 | 0.15 | 0.15 |
| Second agent | Polymerizable monomer (b) having no acid group | D2.6E | 80 | 80 | 80 | 75 | 75 | 75 | 75 | 75 | 80 |
| | Polymerization accelerator (f) | TPBSS | 3 | 3 | 3 | 3 | 3 | 3 | 3 | 3 | 3 |
| | | DEPT | 0.5 | 0.5 | 0.5 | 0.5 | 0.5 | 0.5 | 0.5 | 05 | 0.5 |
| | | BTA | 3 | 3 | 3 | 3 | 3 | 3 | 3 | 3 | 3 |
| | | DMETU | | | | | | | | | |
| | Silane coupling agent (g) | 8-MOS | 20 | | | 20 | 20 | 20 | 20 | 20 | 20 |
| | | 11-MUS | | 20 | | | | | | | |
| | | MPhS | | | 20 | | | | | | |
| | | 11-MUES | | | | | | | | | |
| | Other silane coupling agents | γ-MPS | | | | | | | | | |
| | | γ-MPES | | | | | | | | | |
| | Crosslinking agent (h) | TSPI | | | | | 5 | | | | |
| | | BSB | | | | | | 5 | | | |
| | | BSE | | | | | | | 5 | | |
| | | BSH | | | | | | | | 5 | |
| | | BSO | | | | | | | | | 5 |
| | Filler (e) | F2 (barium glass) | 220 | 220 | 220 | 220 | 220 | 220 | 220 | 220 | 220 |
| | | Alumina | 10 | 10 | 10 | 10 | 10 | 10 | 10 | 10 | 10 |
| | Others | PDE | 0.05 | 0.05 | 0.05 | 0.05 | 0.05 | 0.05 | 0.05 | 0.05 | 0.05 |
| | | BHT | 0.05 | 0.05 | 0.05 | 0.05 | 0.05 | 0.05 | 0.05 | 0.05 | 0.05 |
| Tensile bond strength (MPa) to porcelain | | 37° C., 1 d | 37.2 | 34.4 | 34.8 | 41.1 | 41.8 | 40.7 | 42.6 | 41.5 | 43.2 |
| | | 70° C., 10 d | 25.4 | 27.3 | 24.8 | 30.1 | 31 | 30.2 | 33.8 | 32.2 | 32 |
| Tensile bond strength (MPa) to lithium disilicate glass ceramic | | 37° C., 1 d | 36.4 | 35.5 | 38.9 | 40.2 | 39.3 | 38 | 39.1 | 38.4 | 37.5 |
| | | 70° C., 3 d | 23.5 | 20.3 | 25 | 28.6 | 29.5 | 28.5 | 29.1 | 29.9 | 27 |

TABLE 2

| | | Example 10 | Example 11 | Example 12 | Example 13 | Example 14 | Example 15 | Example 16 | Example 17 | Comparative Example 1 | Comparative Example 2 |
|---|---|---|---|---|---|---|---|---|---|---|---|
| First agent | Polymerizable monomer (a) having an acid group | MDP | 20 | 20 | 20 | 20 | 20 | 20 | 20 | 20 | 20 | 20 |
| | Polymerizable monomer (b) having no acid group | Bis-GMA | 40 | 40 | 40 | 40 | 40 | 40 | 40 | 40 | 40 | 40 |
| | | D2.6E | 25 | 25 | 25 | 25 | 25 | 25 | 25 | 25 | 25 | 25 |
| | | HEMA | 15 | 15 | 15 | 15 | 15 | 15 | 15 | 15 | 15 | 15 |
| | Polymerization initiator (c) | Copper(II) acetate | 0.001 | 0.001 | 0.001 | 0.001 | | | | 0.001 | 0.001 | 0.001 |
| | | VOAA | | | | | | | 0.1 | | | |
| | | BPB | 0.5 | 0.5 | 0.5 | 0.5 | | | | 0.5 | 0.5 | 0.5 |
| | | BPO | | | | | 3 | | | | | |
| | | KPS | | | | | | 2 | | | | |
| | | THP | | | | | | | 4 | | | |
| | Filler (d) | F1 (silica) | 215 | 215 | 215 | 215 | 215 | 215 | 215 | 215 | 215 | 215 |
| | | R972 | 15 | 15 | 15 | 15 | 15 | 15 | 15 | 15 | 15 | 15 |
| | Silanol condensation catalyst (i) | Ti(OBu)$_4$ | 1 | | | | | | | | | |
| | | Ti(C$_3$H$_7$O)$_2$(AcAc)$_2$ | | 1 | | | | | | | | |
| | | Ti(C$_3$H$_7$O)$_2$(C$_6$H$_9$O$_3$)$_2$ | | | 1 | | | | | | | |
| | | Ti(C$_8$H$_{17}$O)$_2$(C$_8$H$_{17}$O$_2$)$_2$ | | | | 1 | | | | | | |
| | | Zr(C$_5$H$_7$O$_2$)$_4$ | | | | | | | | | | |
| | Photopolymerization initiator (j) | CQ | 0.1 | 0.1 | 0.1 | 0.1 | 0.1 | 0.1 | 0.1 | 0.1 | 0.1 | 0.1 |
| | Other | BHT | 0.15 | 0.15 | 0.15 | 0.15 | 0.15 | 0.15 | 0.15 | 0.15 | 0.15 | 0.15 |
| Second agent | Polymerizable monomer (b) having no acid group | D2.6E | 80 | | | | 80 | 80 | 80 | 80 | 80 | 80 |
| | Polymerization accelerator (f) | TPBSS | 3 | | | | 3 | 3 | 3 | 3 | 3 | 3 |
| | | DEPT | 0.5 | | | | 0.5 | 0.5 | 0.5 | 0.5 | 0.5 | 0.5 |
| | | BTA | 3 | | | | | | | 3 | 3 | 3 |
| | | DMETU | | | | | | | | | | |
| | Silane coupling agent (g) | 8-MOS | 20 | | | | 20 | 20 | | | | |
| | | 11-MUS | | | | | | | 4 | | | |
| | | MPhS | | | | | | | 20 | | | |
| | | 11-MUES | | | | | | | | 20 | | |
| | Other silane coupling agents | γ-MPS | | | | | | | | | 20 | |
| | | γ-MPES | | | | | | | | | | |
| | Crosslinking agent (h) | TSPI | | | | | | | | | | 20 |
| | | BSB | | | | | | | | | | |
| | | BSE | | | | | | | | | | |
| | | BSH | | | | | | | | | | |
| | | BSO | | | | | | | | | | |
| | Filler (e) | F2 (barium glass) | 220 | | | | 220 | 220 | 220 | 220 | 220 | 220 |
| | | Alumina | 10 | | | | 10 | 10 | 10 | 10 | 10 | 10 |
| | Others | PDE | 0.05 | | | | 0.05 | 0.05 | 0.05 | 0.05 | 0.05 | 0.05 |
| | | BHT | 0.05 | | | | 0.05 | 0.05 | 0.05 | 0.05 | 0.05 | 0.05 |
| Tensile bond strength (MPa) to porcelain | 37° C., 1 d | | 39.9 | 41.2 | 41.9 | 42.4 | 33.7 | 35.2 | 35.6 | 35 | 30.4 | 33.1 |
| | 70° C., 10 d | | 31.9 | 34 | 33.3 | 32.9 | 27.8 | 29 | 28.6 | 22.3 | 23.7 | 24 |
| Tensile bond strength (MPa) to lithium disilicate glass ceramic | 37° C., 1 d | | 35.6 | 36.7 | 37.8 | 39.9 | 36.7 | 34.9 | 35.5 | 30.8 | 28.8 | 27.9 |
| | 70° C., 3 d | | 27.2 | 27.8 | 27.1 | 28.5 | 22.4 | 22.9 | 24 | 16.2 | 4 | 3.7 |

As shown in Table 1 and Table 2, all of the two-paste dental curable compositions produced in Examples 1 to 17 according to the present invention exhibited high bond durability to porcelain and lithium disilicate glass ceramic just after the production. On the other hand, the two-paste dental curable compositions produced in Comparative Examples 1 and 2 drastically decreased in bond durability to lithium disilicate glass ceramic. In Comparative Example 1, in which the silane coupling agent used is the same as the silane coupling agent disclosed in Example 13 of Patent Literature 3, good bond durability to lithium disilicate glass could not be achieved. The reason is presumably as follows: when a trialkoxysilyl group is hydrolyzed to form a siloxane bond with a silanol group on the surface of a lithium disilicate-containing glass ceramic, a carbon chain between a methacryloxy group and alkoxysilyl group is too short to make an adhesive interface sufficiently hydrophobic and consequently, hydrolysis of the siloxane bond is easily caused by water entry to the adhesive interface. In Comparative Example 2, in which the silane coupling agent used is the same as the silane coupling agent disclosed in Examples 1, 2, and 6 of Patent Literature 1, good bond durability to lithium disilicate glass could not be achieved. As in Comparative Example 1, the reason is presumably that a carbon chain between a methacryloxy group and alkoxysilyl group is too short to make an adhesive interface sufficiently hydrophobic and hydrolysis of a siloxane bond is easily caused by water entry to the adhesive interface.

INDUSTRIAL APPLICABILITY

The two-paste dental curable composition of the present invention can be suitably used for dental restorative treatment. Moreover, the two-paste dental curable composition of the present invention can be suitably used as a dental cement and can be particularly suitably used as a self-adhesive dental cement. Furthermore, the two-paste dental curable composition of the present invention can be particularly suitably used as a dental cement used for lithium disilicate glass.

The invention claimed is:

1. A two-paste dental curable composition, comprising:
a first agent comprising a polymerizable monomer (a) comprising an acid group, a polymerizable monomer (b) having no acid group, a polymerization initiator (c), and a filler (d); and
a second agent comprising a polymerizable monomer (b) comprising no acid group, at least one filler (e) selected from the group consisting of a lanthanum glass, barium glass, strontium glass, soda glass, zinc glass, fluoroaluminosilicate glass, and alumina, a polymerization accelerator (f), and a silane coupling agent (g) of formula (I):

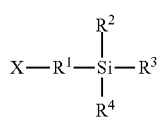

(I)

wherein
X is a polymerizable (meth)acryloxy group, vinyl group, or epoxy group,
$R^1$ is a divalent aliphatic group optionally comprising a divalent group and comprising a linear chain with a carbon chain length of 5 or more or a divalent aromatic group optionally comprising a divalent group and comprising 6 or more carbon atoms, $R^2$, $R^3$, and $R^4$ are each independently a hydroxy group, an alkyl group comprising 1 to 5 carbon atoms, or an alkoxy group comprising 1 to 5 carbon atoms, and at least one of $R^2$, R.', and $R^4$ is an alkoxy group comprising 1 to 5 carbon atoms, wherein, in the first agent, the polymerization initiator (c) comprises an inorganic peroxide (c-1) or a transition metal complex (c-2), the inorganic peroxide (c-1) comprising at least one selected from the group consisting of peroxodisulfuric acid salt and peroxodiphosphoric acid salt, and the transition metal complex (c-2) comprising at least one selected from the group consisting of a copper compound and vanadium compound.

2. The composition of claim 1, wherein $R^1$ is a divalent aliphatic group optionally comprising a divalent group and comprising a linear chain with a carbon chain length of 7 or more or a divalent aromatic group optionally comprising a divalent group and comprising 7 or more carbon atoms.

3. The composition of claim 1, wherein
$R^2$, $R^3$, and $R^4$ are each independently a hydroxy group, an alkyl group comprising 1 to 3 carbon atoms, or an alkoxy group comprising 1 to 3 carbon atoms and
at least one of $R^2$, $R^3$, and $R^4$ is an alkoxy group comprising 1 to 3 carbon atoms.

4. The composition of claim 1, wherein
$R^2$, $R^3$, and $R^4$ are each independently a hydroxy group, a methyl group, or a methoxy group, and
at least one of $R^2$, $R^3$, and $R^4$ is a methoxy group.

5. The composition of claim 1, wherein $R^2$, $R^3$, and $R^4$ are each a methoxy group.

6. The composition of claim 1, wherein $R^1$ is a divalent aliphatic group optionally comprising a divalent group and comprising a linear chain with a carbon chain length of 8 or more.

7. The composition of claim 1, wherein $R^1$ is a divalent aromatic group optionally comprising a divalent group and comprising 8 or more carbon atoms.

8. The composition of claim I, wherein the silane coupling agent (g) is at least one selected from the group consisting of 5-(meth)acryloxypentyltrimethoxysilane, 6-(meth)acryloxyhexyltrimethoxysilane, 7-(meth)acryloxyheptyltrimethoxysilane, 8-(meth)acryloxyoctyltrimethoxysilane, 9-(meth)acryloxyrionyhrimethoxysilane, 10-(meth)acryloxydecyltrimethoxysilane, 11-(meth)acryloxyundecyltrimethoxysilane, 8-(meth)acryloxyoctylmethyldimethoxysilane, 10-(meth)acryloxydecylmethyldimethoxysilane, 11-(meth)acryloxyundecylmethyldimethoxysilane, and (meth)acryloxymethylphenethyltrimethoxysilane.

9. The composition of claim 1, wherein the silane coupling agent (g) is at least one selected from the group consisting of 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, and (meth)acryloxymethylphenethyltrimethoxysilane.

10. The composition of claim 1, wherein the second agent further comprises a crosslinking agent (h), and
wherein the crosslinking agent (h) is a compound of formula (V):

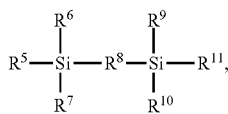

and/or
a compound of formula (V1):

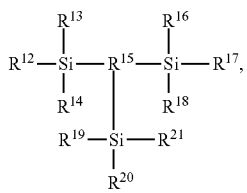

wherein
- R⁸ is a divalent aliphatic group optionally comprising a divalent group and having a carbon chain length of 1 or more or a divalent aromatic group optionally comprising a divalent group and comprising 6 or more carbon atoms,
- R¹⁵ is a trivalent aliphatic group having a carbon chain length of 1 or more or a trivalent aromatic group optionally comprising a divalent group and comprising 6 or more carbon atoms, and
- R⁵ to R⁷, R⁹ to R¹⁴, and R¹⁶ to R²¹ are each independently a hydroxy group or an alkoxy group comprising 1 to 5 carbon atoms.

11. The composition of claim 10, wherein
- R⁸ is a divalent aromatic group optionally comprising a divalent group and comprising 6 or more carbon atoms and
- R¹⁵ is a trivalent aromatic group optionally comprising a divalent group and comprising 6 or more carbon atoms.

12. The composition of claim 10, wherein the crosslinking agent (h) is the compound of formula (V), and
wherein R⁸ is a divalent aliphatic group optionally comprising a divalent group and having a carbon chain length of 1 or more.

13. The composition of claim 1, wherein the first agent further comprises a silanol condensation catalyst (i) of formula (VII):
M(R²²)ₙ (VII), wherein
M is Ti, Zr, or Al,
R²² is an aliphatic group,
n is an integer in a range of from 1 to 4 plural R²² optionally differing from each other.

14. The composition of claim 13, wherein R²² is an alkoxy group comprising 1 to 9 carbon atoms, an acyloxy group comprising 2 to 9 carbon atoms, an alkenyloxy group comprising 3 to 9 carbon atoms, a β-diketonate group comprising 5 to 15 carbon atoms, or a diacylmethyl group having acyl groups each comprising 1 to 9 carbon atoms.

15. The composition of claim 1, wherein the first agent and/or the second agent further comprises a photopolymerization initiator (j).

16. The composition of claim 1, wherein the filler (e) is the barium glass and/or the alumina.

17. The composition of claim 1, which is suitable for application to a biological hard tissue.

18. The composition of claim 1, a tensile bond strength to lithium disilicate glass ceramic at a temperature of 70° C. after 3 days in a range of from 16.2 to 28,5 MPa.

19. The composition of claim 1, wherein the silane coupling agent (g) comprises 8-(meth)acryloxyoctyltrimethoxyvsilane, 9-(meth)acryloxynonyltrimethoxysilane, 10-(meth)acryloxydecyltrimethoxysilane, 11-(meth)acryloxyundecyltrimethoxysilane, and/or (meth)acryloxymethylphenethylnimethoxysilane.

20. A two-paste dental curable composition, comprising:
a first agent comprising (a) a polymerizable monomer comprising an acid group, (b) a polymerizable monomer having no acid group, (c) a polymerization initiator, and (d) a filler; and
a second agent comprising (b) a polymerizable monomer comprising no acid group, (e) a basic glass filler and alumina, (f) a polymerization accelerator, and (g) a silane coupling agent of formula (1):

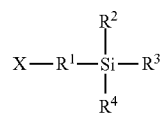

wherein
X is a polyrnerizable (meth)acryloxy group, vinyl group, or epoxy group,
R¹ is a divalent aliphatic group optionally comprising a divalent group and comprising a linear chain with a carbon chain length of 5 or more or a divalent aromatic group optionally comprising a divalent group and comprising 6 or more carbon atoms,
R², R³, and R⁴ are each independently a hydroxy group, an alkyl group comprising 1 to 5 carbon atoms, or an alkoxy group comprising 1 to 5 carbon atoms, and at least one of R², R³, and R⁴ is an alkoxy group comprising 1 to 5 carbon atoms,
wherein the second agent further comprises a crosslinking agent (h), and
wherein the crosslinking agent (h) is a compound of formula (V) and/or a compound of formula (VI):

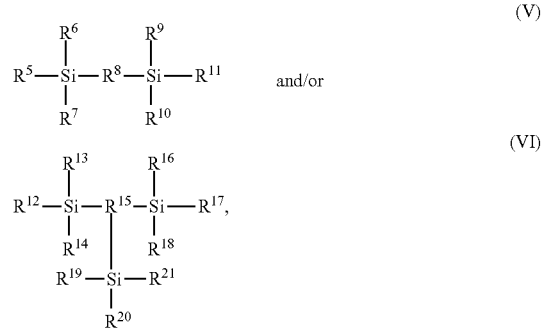

wherein
R⁸ is a divalent aliphatic group optionally comprising a divalent group and having a carbon chain length of 1 or more or a divalent aromatic group optionally comprising a divalent group and comprising 6 or more carbon atoms, $R^{15}$ is a trivalent aliphatic group having a carbon chain length of 1 or more or a trivalent aromatic group optionally comprising a divalent group and comprising 6 or more carbon atoms, and $R^5$ to $R^7$, $R^9$ to $R^{14}$, and $R^{16}$ to $R^{21}$ are each independently a hydroxy group or an alkoxy group comprising 1 to 5 carbon atoms.

* * * * *